United States Patent
Gurney et al.

(10) Patent No.: US 11,028,050 B2
(45) Date of Patent: Jun. 8, 2021

(54) SALTS AND POLYMORPHS OF A PDE4 INHIBITOR

(71) Applicant: TETRA DISCOVERY PARTNERS, INC., Grand Rapids, MI (US)

(72) Inventors: Mark E. Gurney, Grand Rapids, MI (US); Jon P. Lawson, Wildwood, MO (US); Stephan D. Parent, West Lafayette, IN (US); Richard James Ely, Williamsport, IN (US)

(73) Assignee: TETRA DISCOVERY PARTNERS, INC., Grand Rapids, MI (US)

( * ) Notice: Subject to any disclaimer, the term of this patent is extended or adjusted under 35 U.S.C. 154(b) by 0 days.

(21) Appl. No.: 16/851,203

(22) Filed: Apr. 17, 2020

(65) Prior Publication Data

US 2020/0331858 A1   Oct. 22, 2020

Related U.S. Application Data

(60) Provisional application No. 62/835,867, filed on Apr. 18, 2019.

(51) Int. Cl.
*C07D 213/55*   (2006.01)

(52) U.S. Cl.
CPC ........ *C07D 213/55* (2013.01); *C07B 2200/13* (2013.01)

(58) Field of Classification Search
CPC .......................... C07D 213/55; C07B 2200/13
See application file for complete search history.

(56) References Cited

U.S. PATENT DOCUMENTS

2015/0119362 A1* 4/2015 Gurney ................ C07D 213/74
514/64

FOREIGN PATENT DOCUMENTS

WO   WO-2014/066659 A1   5/2014

OTHER PUBLICATIONS

Barad et al., Rolipram, a Type IV-specific Phosphodiesterase Inhibitor, Facilitates the Establishment of Long-Lasting Long-Term Potentiation and Improves Memory, Proc. Natl. Acad. Sci. USA, 95(25):15020-5 (1998).
Cui et al., Protection From Amyloid beta Peptide-Induced Memory, Biochemical, and Morphological Deficits by a Phosphodiesterase-4D Allosteric Inhibitor, J. Pharmacol. Exp. Ther., 371(2):250-259 (Nov. 2019).
Frey et al., Effects of cAMP Simulate a Late Stage of LTP in Hippocampal CA1 Neurons, Science, 260(5114):1661-4 (1993).
Gurney et al., Design and Synthesis of Selective Phosphodiesterase 4D (PDE4D) Allosteric Inhibitors for the Treatment of Fragile X Syndrome and Other Brain Disorders, J. Med. Chem., 62(10):4884-901 (May 2019).
Hölzer et al., K[alpha]1,2 and K[beta]1,3 x-ray emission lines of the 3d transition metals, Phys. Rev. A 56, 4554 (Dec. 1997).
International Application No. PCT/US2020/028616, International Search Report and Written Opinion, dated Jun. 16, 2020.
Ohm et al., Decrease in Adenylate Cyclase Activity Antecedes Neurofibrillary Tangle Formation, Neurobiol. Aging, 18(3):275-9 (May-Jun. 1997).
Rose et al., Phosphodiesterase Inhibitors for Cognitive Enhancement, Curr. Pharm. Des., 11(26):3329-34 (2005).

* cited by examiner

*Primary Examiner* — Timothy R Rozof

(74) *Attorney, Agent, or Firm* — Marshall, Gerstein & Borun LLP

(57) ABSTRACT

Provided herein are free base crystalline forms and crystalline salts of Compound 1.

16 Claims, 15 Drawing Sheets

SALTS AND POLYMORPHS OF A PDE4 INHIBITOR

BACKGROUND

It is known that cAMP-specific phosphodiesterase-4 (PDE4) is an enzyme related to second messenger cAMP regulation and deeply related to learning and memory functions (Science 1993, 260: 1661-4). It has been shown that PDE4 inhibitors promote neuronal plasticity in vitro, and improve or promote learning and memory in various models in vivo (PNAS 1998, 95: 15020-5; Current Pharmaceutical Design 2005, 11: 3329-34). Further, cAMP synthetic enzyme activity is decreased in AD patients and decrease in cAMP signal transduction in a pathological condition can be assumed (Neurobiol Aging 1997, 18: 275-9). PDE4BD is one isoform of PDE4 and has been implicated in the etiology in a host of different diseases.

The compound, 2-(4-((2-(3-chlorophenyl)-6-(trifluoromethyl)pyridin-4-yl)methyl)phenyl)-1-(l1-oxidaneyl)ethan-1-one ("Compound 1"), is useful as a PDE4 inhibitor, and is undergoing clinical trials as a therapy for Fragile X Syndrome:

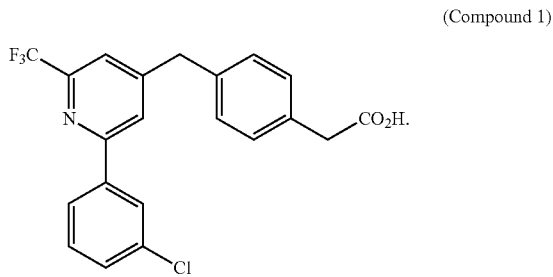 [SMILES: O=C(O)Cc1ccc(Cc2cc(-c3cccc(Cl)c3)nc(C(F)(F)F)c2)cc1]

(Compound 1)

There is a need for salts and crystalline forms of Compound 1 with different chemical and physical stabilities, and formulations and uses of the same.

SUMMARY

Provided herein are crystalline forms and salts of Compound 1, including free base crystalline forms and crystalline salts. In some embodiments, provided herein is the crystalline form of free base Compound 1 (Form A). In some embodiments, provided herein is the crystalline form of Compound 1 and p-dioxane (Form B). In some embodiments, provided herein is the crystalline form of Compound 1 and dichloromethane (Form C). In some embodiments, provided herein is the crystalline form of a Compound 1 calcium salt (Form D). In some embodiments, provided herein is the crystalline form of a Compound 1 potassium salt (Form E). In some embodiments, provided herein is the crystalline form of a Compound 1 potassium salt (Form F). In some embodiments, provided herein is the crystalline form of a Compound 1 sodium salt (Form G). In some embodiments, provided herein is the crystalline form of a Compound 1 sodium salt (Form H).

Also provided are pharmaceutical compositions comprising a crystalline form of Compound 1 or salt thereof as disclosed herein and a pharmaceutically acceptable carrier.

Further provided are methods of treating a PDE4D related disorder in a subject in need thereof comprising administering to the subject the crystalline form as disclosed herein in an amount effective to threat the PDE4D related disorder.

DETAILED DESCRIPTION

The present disclosure provides salts and polymorphs of 2-(4-((2-(3-chlorophenyl)-6-(trifluoromethyl)pyridin-4-yl)methyl)phenyl)-1-(l1-oxidaneyl)ethan-1-one, termed "Compound 1" herein, and having a structure of:

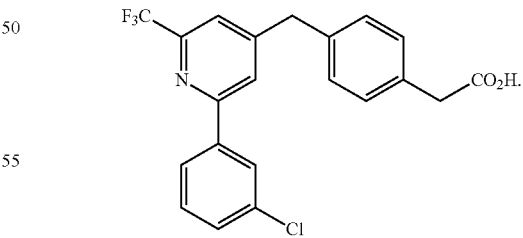

Embodiments of the free base forms and salt forms of Compound 1 can be characterized by one or more of the parameters described in further detail below.

Free Base Crystalline Forms of Compound I

Provided herein are free base crystalline forms of Compound 1. In embodiments, the free base crystalline forms of Compound 1 can be nonionic forms of Compound 1. In embodiments, the free base crystalline forms of Compound 1 can be a solvate. In embodiments, the free base crystalline forms of Compound 1 can be anhydrous.

Free Base Anhydrous Crystalline Form A

Figure 1:
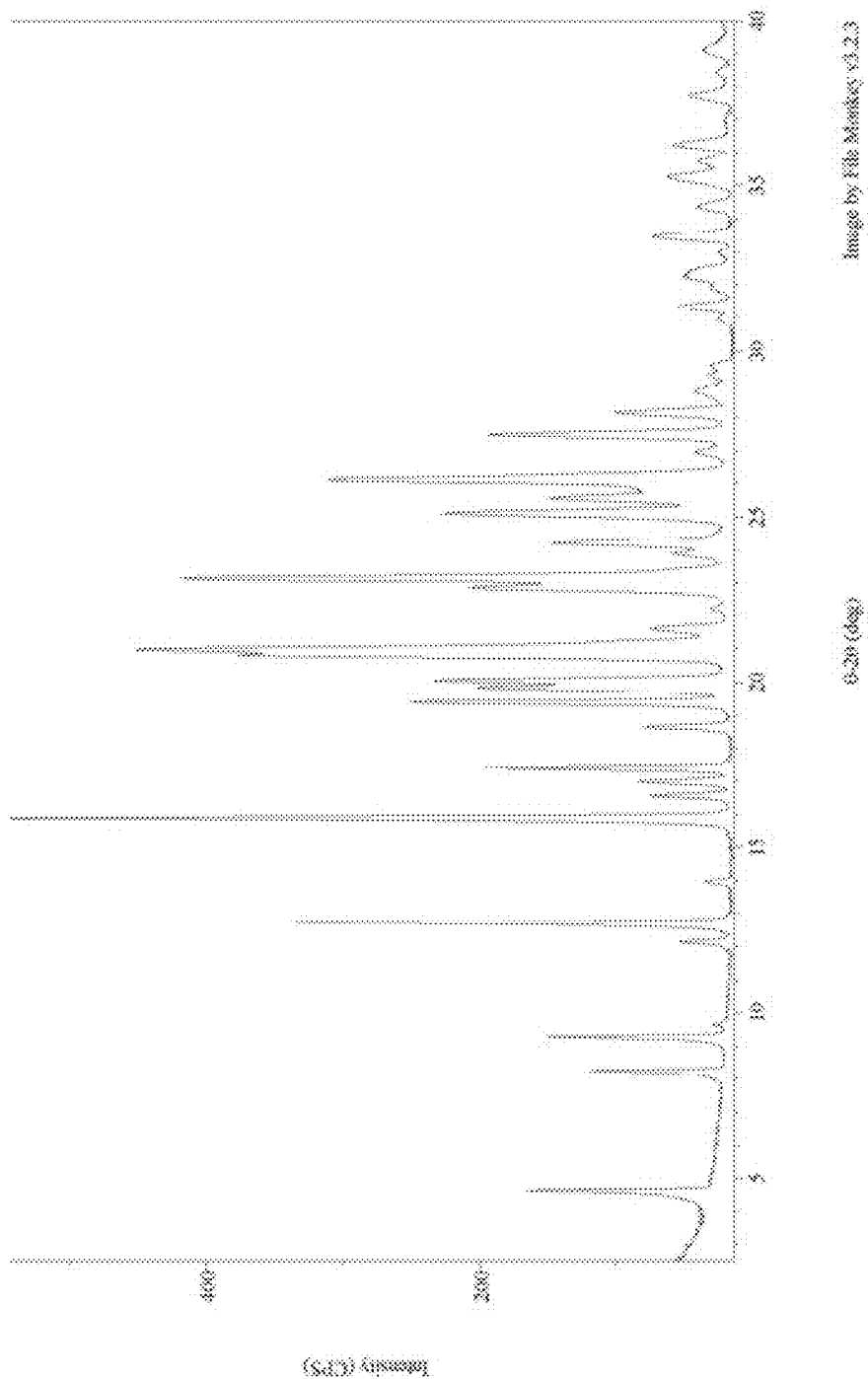
FIG. 1 depicts an X-ray powder diffraction ("XRPD") pattern of Compound 1 free base anhydrous crystalline Form A.

Free base anhydrous crystalline Form A of Compound 1 ("Form A") can be characterized by an X-ray powder diffraction pattern, obtained as set forth in the Examples, having peaks at about 12.72, 15.90, 19.39, 20.80, 20.98, 23.15, and 26.08±0.2° 2θ using Cu Kα radiation. Form A optionally can be further characterized by an X-ray powder diffraction pattern having additional peaks at about 4.63, 17.40, 19.85, 20.07, 22.84, 25.10, and 27.47±0.2° 2θ using Cu Kα radiation. Form A optionally can be further characterized by an X-ray powder diffraction pattern having additional peaks at about 8.24, 9.29, 16.97, 18.65, 21.19, 21.59, 23.89, 24.20, 25.55, 25.82, and 28.14±0.2°2θ using Cu Kα radiation. Form A optionally can be characterized by an X-ray powder diffraction pattern having peaks shown in Table 2 set forth in the Examples. In some embodiments, Form A has an X-ray powder diffraction pattern substantially as shown in FIG. 1, wherein by "substantially" is meant that the reported peaks can vary by about ±0.2°. It is well known in the field of XRPD that while relative peak heights in spectra are dependent on a number of factors, such as sample preparation and instrument geometry, peak positions are relatively insensitive to experimental details.

Figure 2:
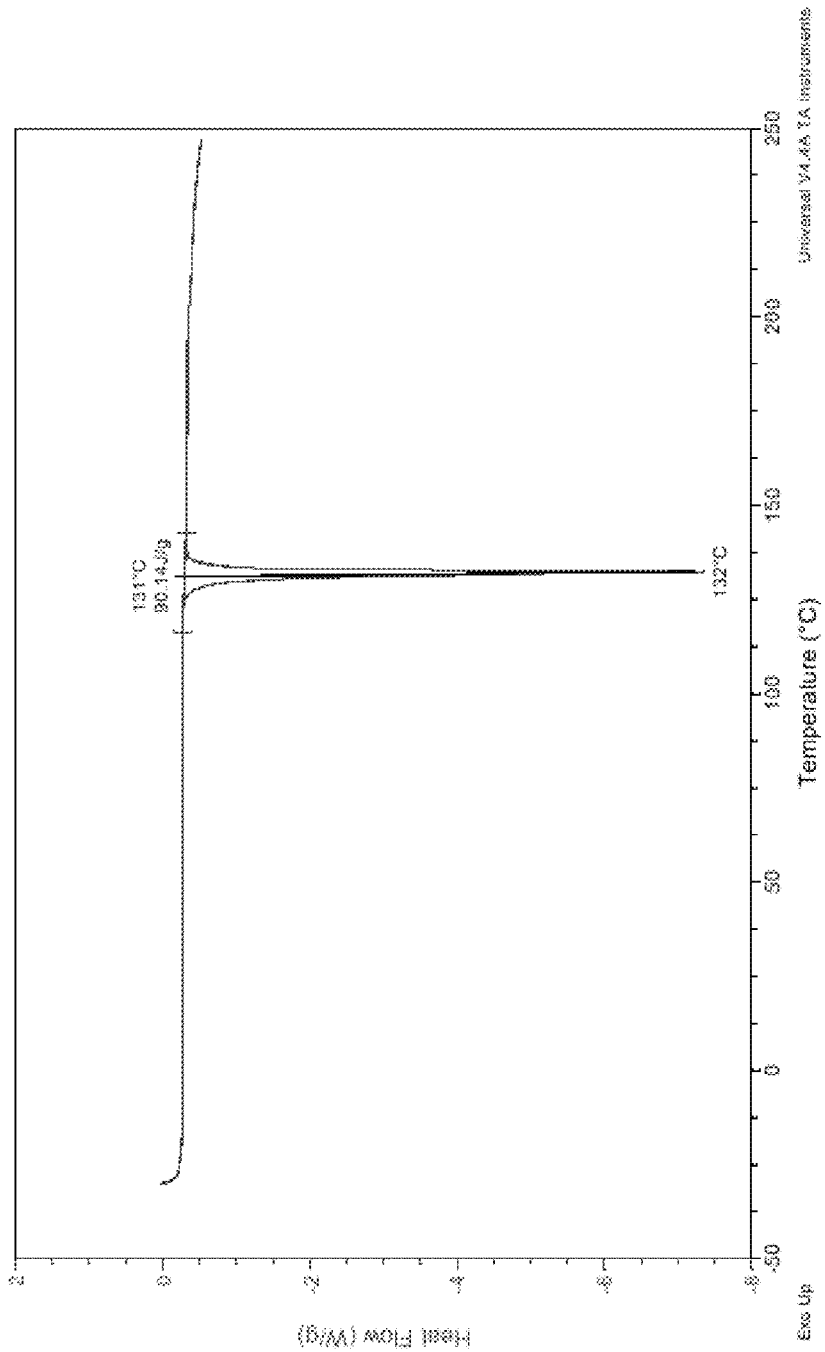
FIG. 2 depicts a differential scanning calorimetry ("DSC") thermograph of Compound 1 free base anhydrous crystalline Form A.

Differential scanning calorimetry (DSC) thermographs were obtained, as set forth in the Examples, for Form A. The DSC curve indicates an endothermic transition at about 131° C.±3° C. Thus, in some embodiments, Form A can be characterized by a DSC thermograph having a solid-solid transition endotherm with an onset in a range of about 125° C. to about 135° C. For example, in some embodiments Form A is characterized by DSC, as shown in FIG. 2.

Figure 3:
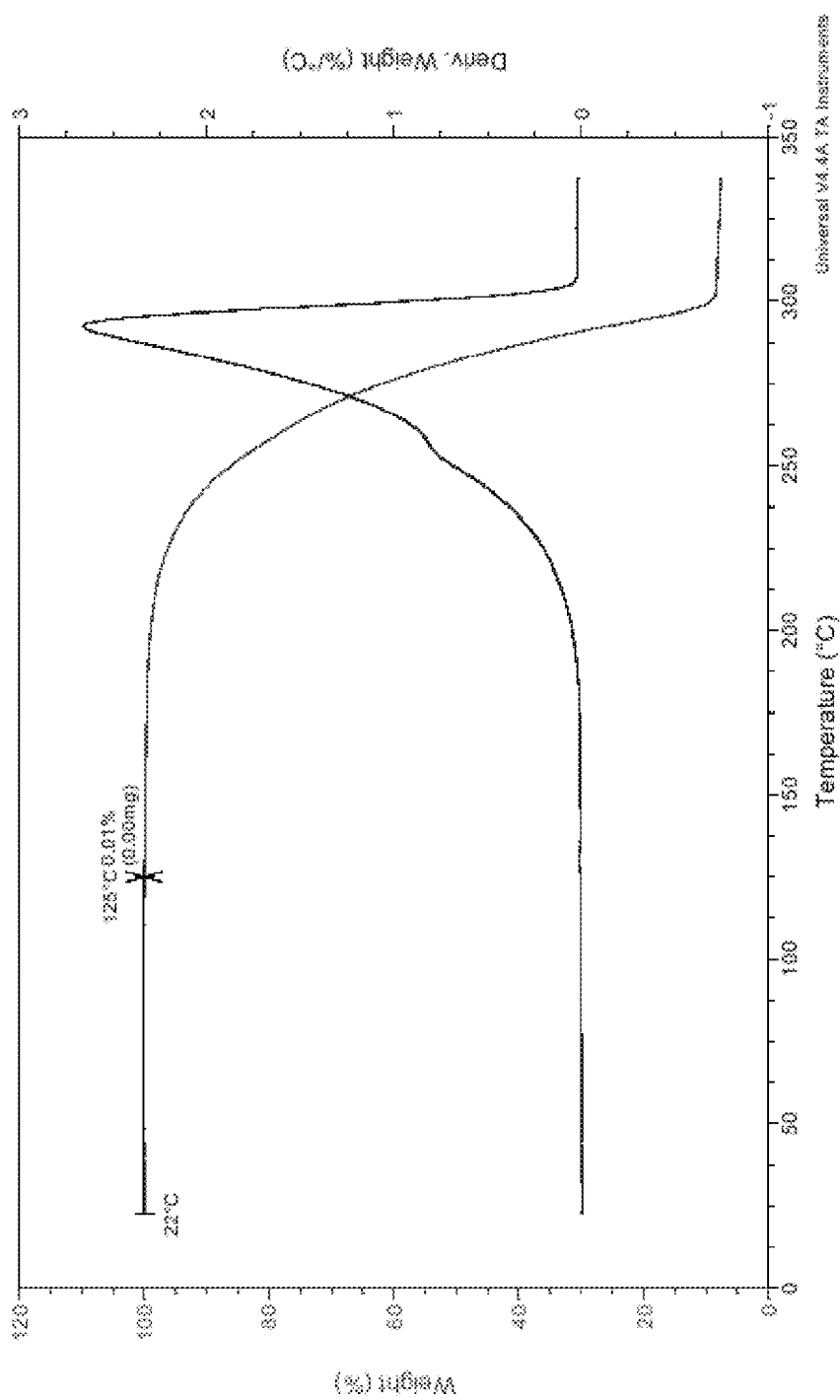
FIG. 3 depicts a thermogravimetric analysis ("TGA") trace of Compound 1 free base anhydrous crystalline Form A.
Figure 4:
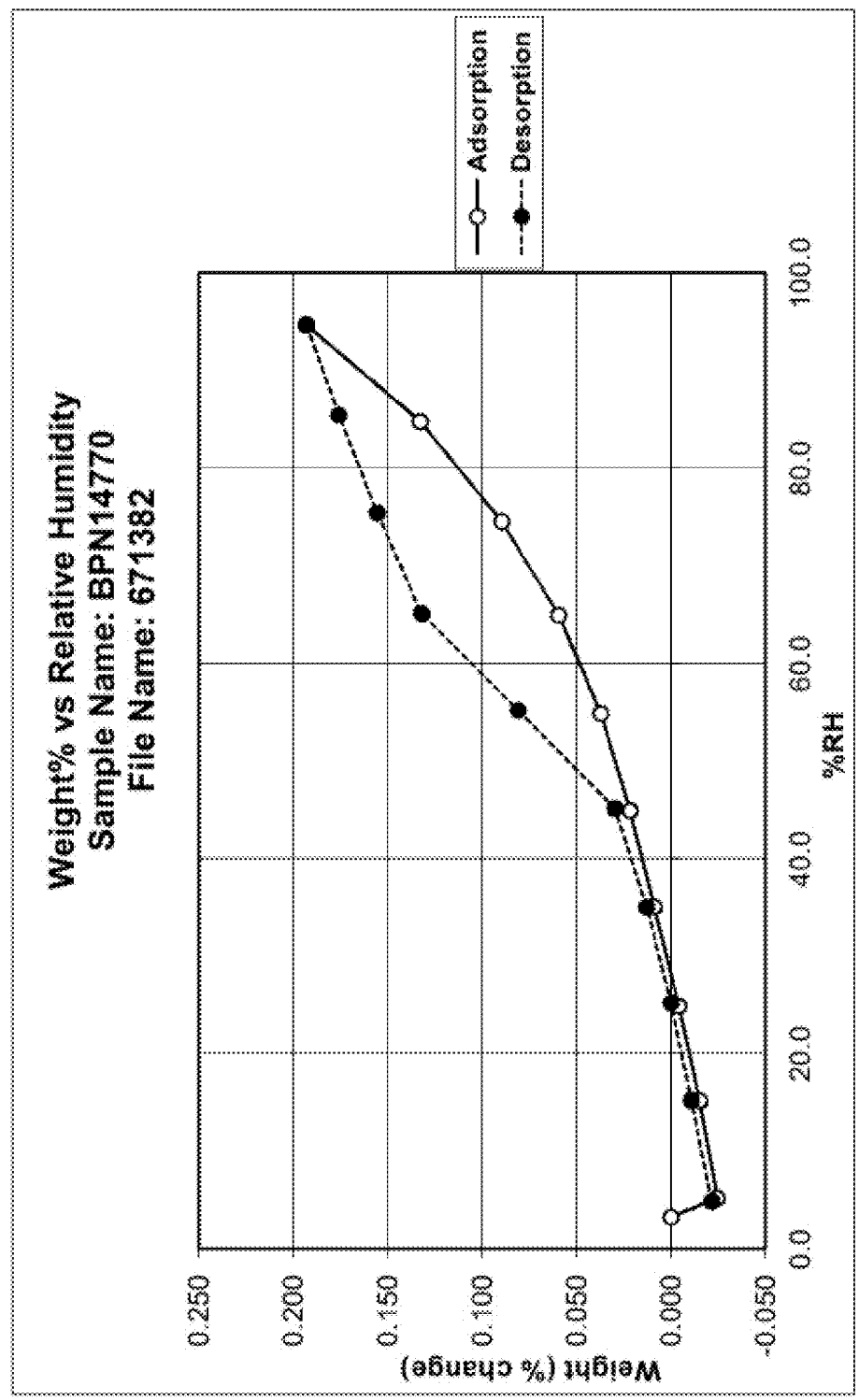
FIG. 4 depicts a dynamic vapor sorption ("DVS") graph of Compound 1 free base anhydrous crystalline Form A.

Form A also can be characterized by thermogravimetric analysis (TGA). Thus, Form A can be characterized by a weight loss in the range of about 0% to about 1% and an onset of decomposition in a range of about 270° C. to 282° C., such as 276° C. In some embodiments, Form A has a thermogravimetric analysis substantially as depicted in FIG. 3, wherein by "substantially" is meant that the reported TGA features can vary by about ±5° C. In embodiments, Form A has a dynamic vapor sorption ("DVS") substantially as shown in FIG. 4.

Free Base Crystalline Form B

Figure 5:
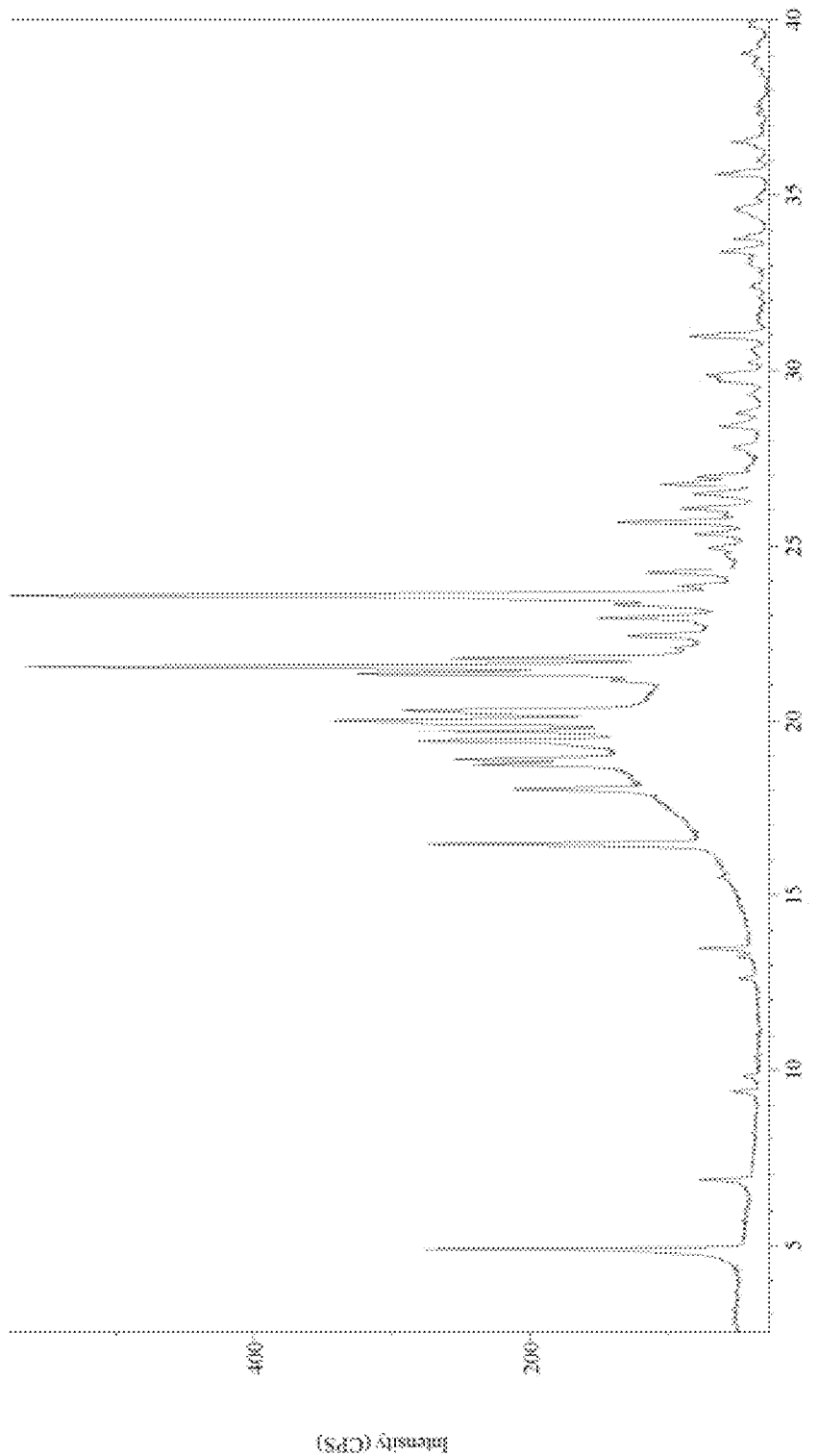
FIG. 5 depicts an X-ray powder diffraction ("XRPD") pattern of Compound 1 the free base crystalline Form B.

Free base crystalline Form B of Compound 1 and p-dioxane ("Form B") can be characterized by an X-ray powder diffraction pattern, obtained as set forth in the Examples, having peaks at about 20.02, 20.29, 21.32, 21.51, and 23.57 ±0.2° 2θ using Cu Kα radiation. Form B optionally can be further characterized by an X-ray powder diffraction pattern having additional peaks at about 4.90, 16.46, 18.03, 18.74, 18.89, 19.39, 19.71, and 21.75±0.2° 2θ using Cu Kα radiation. Form B optionally can be further characterized by an X-ray powder diffraction pattern having additional peaks at about 18.03, 21.14, 22.43, 22.93, 23.29, 23.83, 24.22, 25.65, 26.02, and 26.77±0.2° 2θ using Cu Kα radiation. Form B optionally can be characterized by an X-ray powder diffraction pattern having peaks shown in Table 3 set forth in the Examples. In some embodiments, Form B has an X-ray powder diffraction pattern substantially as shown in FIG. 5, wherein by "substantially" is meant that the reported peaks can vary by about ±0.2°. Form B can be characterized as a mono-dioxane solvate.

Free Base Crystalline Form C

Figure 6:
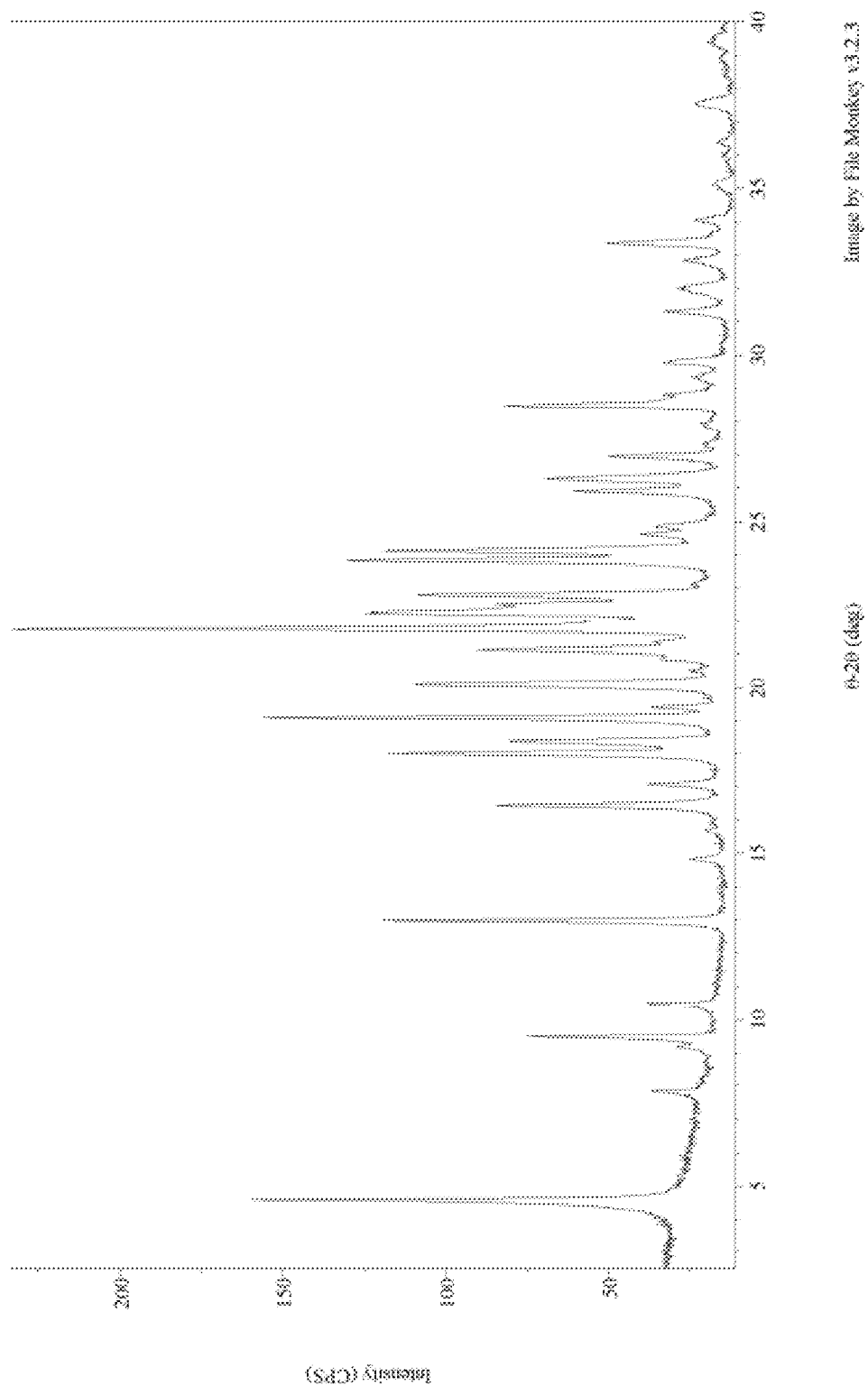
FIG. 6 depicts an X-ray powder diffraction ("XRPD") pattern of Compound 1 free base crystalline Form C.

Free base crystalline Form C of Compound 1 and dichloromethane ("Form C") can be characterized by an X-ray powder diffraction pattern, obtained as set forth in the Examples, having peaks at about 4.59, 13.00, 19.09, 21.74, 22.27, 23.82, and 24.11±0.2° 2θ using Cu Kα radiation. Form C optionally can be further characterized by an X-ray powder diffraction pattern having additional peaks at about 9.50, 16.44, 18.01, 18.38, 20.11, 21.13, 22.51, 22.80, and 28.46±0.2° 2θ using Cu Kα radiation. Form C optionally can be further characterized by an X-ray powder diffraction pattern having additional peaks at about 7.82, 9.20, 10.50, 14.81, 17.05, 19.38, 20.87, 21.36, 24.63, 24.87, 28.79, and 29.80±0.2° 2θ using Cu Kα radiation. Form C optionally can be characterized by an X-ray powder diffraction pattern having peaks shown in Table 4 set forth in the Examples. In some embodiments, Form C has an X-ray powder diffraction pattern substantially as shown in FIG. 6, wherein by "substantially" is meant that the reported peaks can vary by about ±0.2°. Form C can be characterized as a mono-dichloromethane (DCM) solvate. In embodiments, Form C can have a ratio of 1 to 1 of Compound 1 to mono-dichloromethane.

Figure 7:
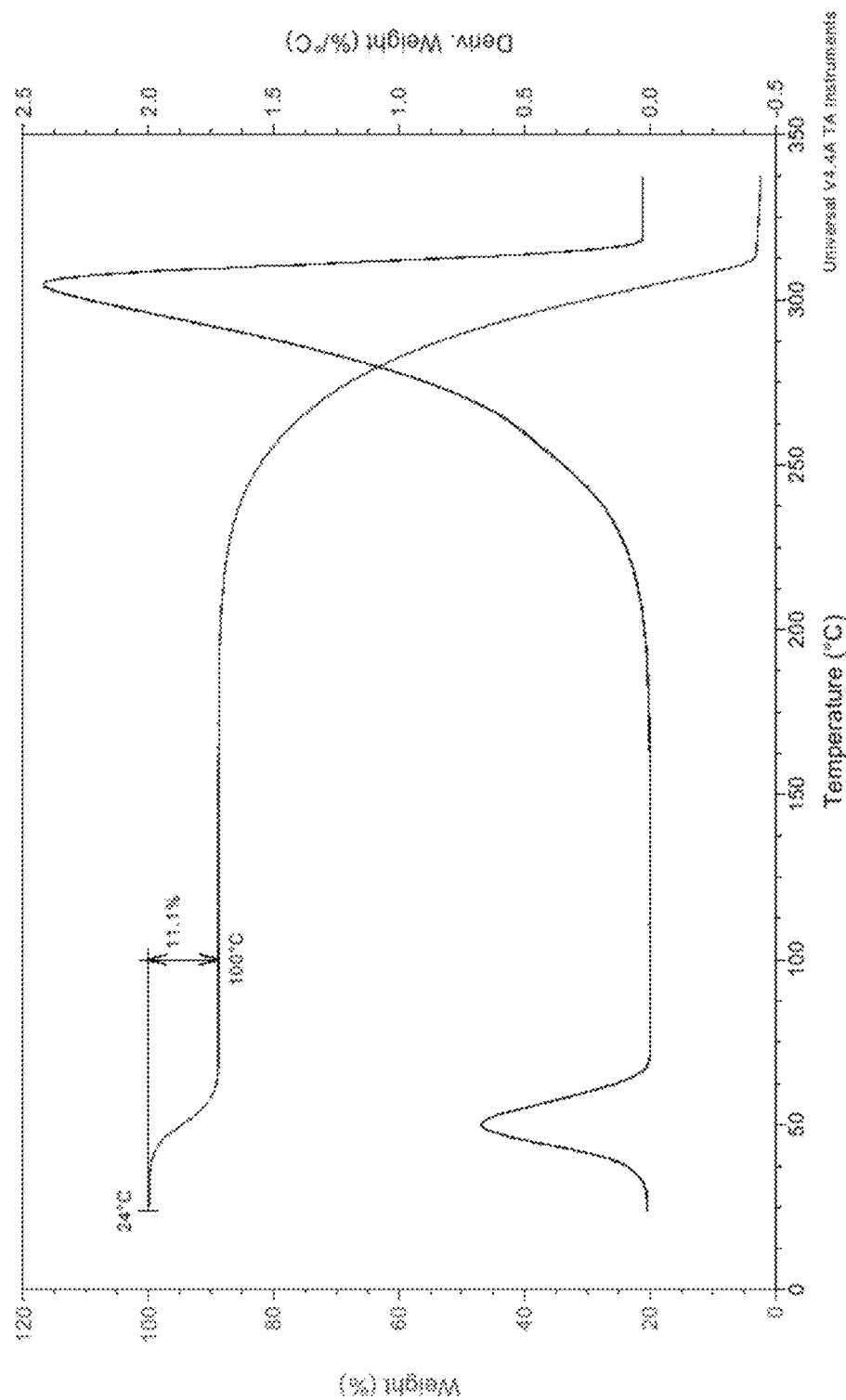
FIG. 7 depicts a thermogravimetric analysis ("TGA") trace of Compound 1 free base crystalline Form C.

Form C also can be characterized by thermogravimetric analysis (TGA). Thus, Form C can be characterized by a weight loss in a range of about 9% to about 12% with an onset temperature in a range of about 40° C. to about 60° C. For example, Form C can be characterized by a weight loss of about 11.1%, up to about 100° C. In some embodiments, Form C has a thermogravimetric analysis substantially as depicted in FIG. 7, wherein by "substantially" is meant that the reported TGA features can vary by about ±5° C.

Compound 1 Salts

Crystalline Calcium Salt Form D

Figure 8:
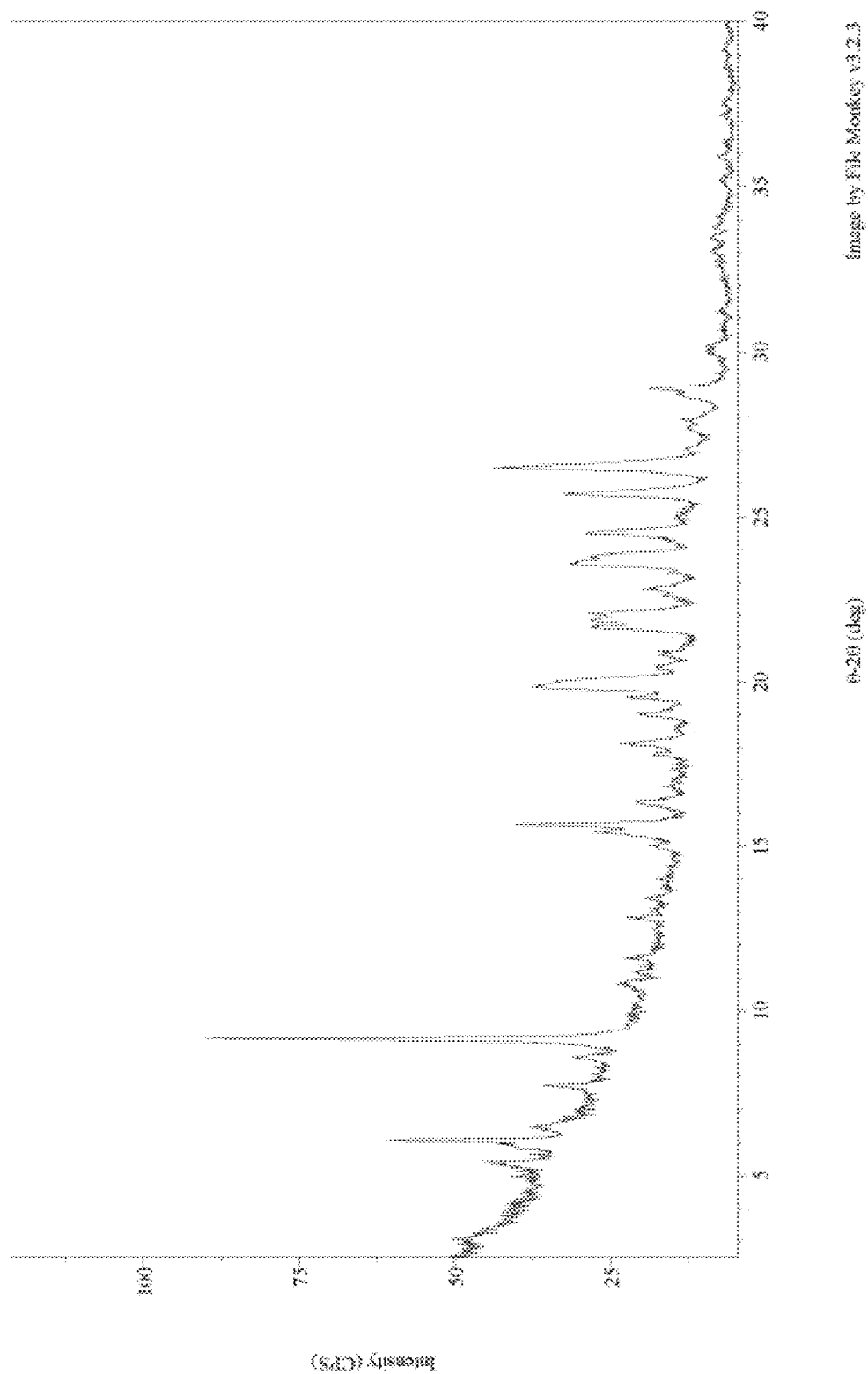
FIG. 8 depicts an X-ray powder diffraction ("XRPD") pattern of Compound 1 crystalline calcium salt Form D.

Crystalline form of Compound 1 calcium salt ("Form D") can be characterized by an X-ray powder diffraction pattern, obtained as set forth in the Examples, having peaks at about 6.10, 9.17, 15.68, 19.86, and 26.46±0.2° 2θ using Cu Kα radiation. Form D optionally can 5.41, 6.49, 7.70, 8.60, 10.86, 12.84, 15.46, 15.68, 19.86, 21.62, 21.84, 22.03, 23.57, 23.75, 24.53, 25.67, and 26.46±0.2° 2θ using Cu Kα radiation. Form D optionally can be further characterized by an X-ray powder diffraction pattern having additional peaks at about 8.74, 16.08, 19.81, and 28.58±0.2° 2θ using Cu Kα radiation. Form D optionally can be characterized by an X-ray powder diffraction pattern having peaks shown in Table 6 set forth in the Examples. In some embodiments, Form D has an X-ray powder diffraction pattern substantially as shown in FIG. 8, wherein by "substantially" is meant that the reported peaks can vary by about ±0.2°.

Crystalline Potassium Salt Form E

Figure 9:
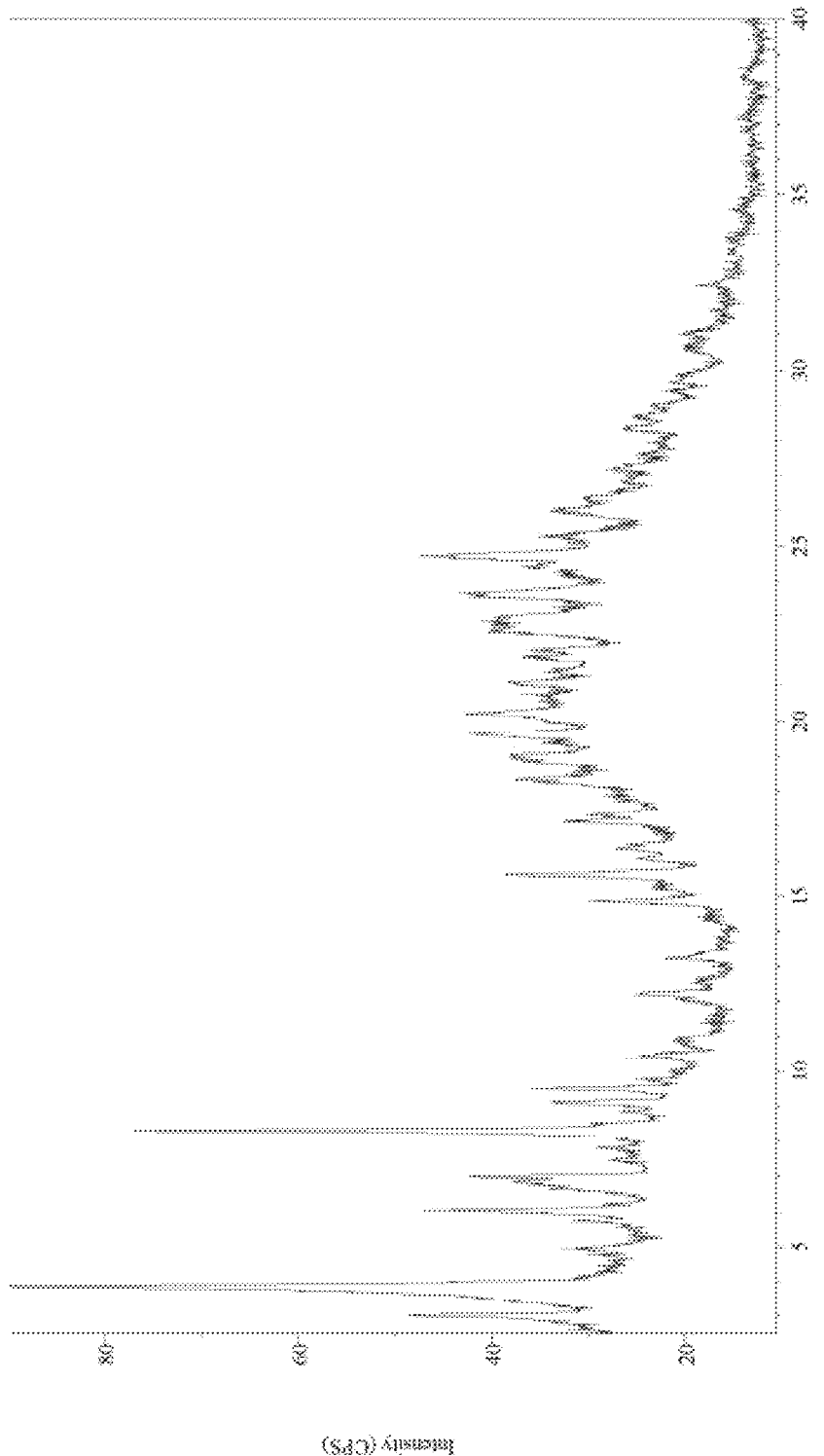
FIG. 9 depicts an X-ray powder diffraction ("XRPD") pattern of Compound 1 crystalline potassium salt Form E.

Crystalline form of Compound 1 potassium salt ("Form E") can be characterized by an X-ray powder diffraction pattern, obtained as set forth in the Examples, having peaks at about 3.02, 3.88, 6.07, 7.01, and 8.32±0.2° 2θ using Cu Kα radiation. Form E optionally can 6.86, 15.63, 18.35, 19.00, 19.64, 20.22, 21.08, 21.79, 22.03, 22.60, 22.93, 23.61, and 24.71±0.2° 2θ using Cu Kα radiation. Form E optionally can be further characterized by an X-ray powder diffraction pattern having additional peaks at about 7.79, 8.87, 9.12, 9.51, 9.77, 10.44, 12.19, 14.85, 16.08, 16.36, 17.10, 17.30, 25.29, and 25.99±0.2° 2θ using Cu Kα radiation. Form E optionally can be characterized by an X-ray powder diffraction pattern having peaks shown in Table 7 set forth in the Examples. In some embodiments, Form E has an X-ray powder diffraction pattern substantially as shown in FIG. 9, wherein by "substantially" is meant that the reported peaks can vary by about ±0.2°.

Crystalline Potassium Salt Form F

Figure 10:
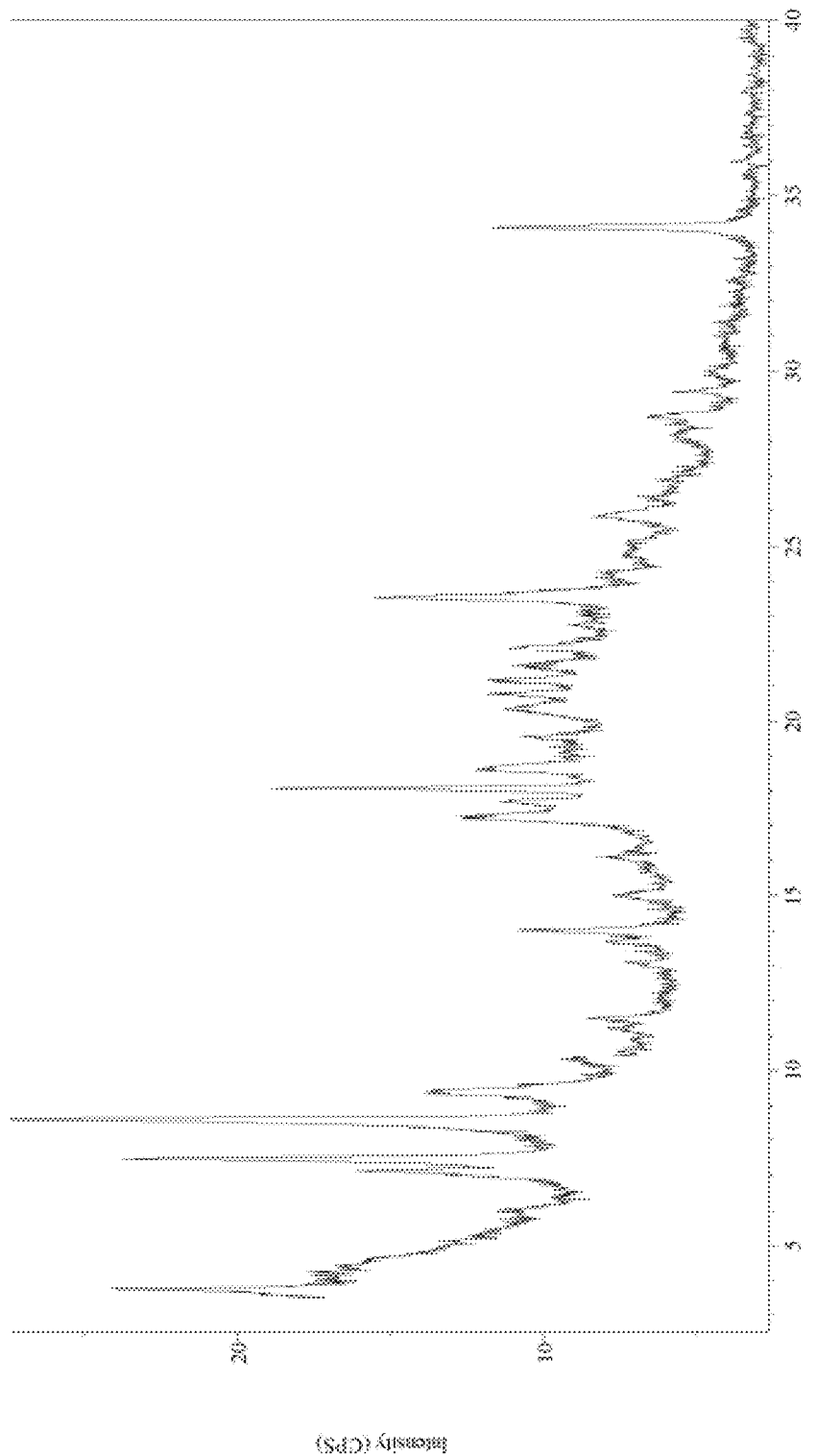
FIG. 10 depicts an X-ray powder diffraction ("XRPD") pattern of Compound 1 crystalline potassium salt Form F.

Crystalline form of Compound 1 potassium salt ("Form F") can be characterized by an X-ray powder diffraction pattern, obtained as set forth in the Examples, having peaks at about 3.8, 7.1, 7.5, 8.6, 9.4, 18.1, and 23.5±0.2° 2θ using Cu Kα radiation. Form F optionally can 10.3, 11.2, 11.5, 13.1, 13.7, 14.0, 15.0, 16.1, 17.2, 17.7, 18.6, 19.5, 20.3, 20.8, 21.1, 21.5, 22.1, 25.9, 28.7 and 29.4±0.2° 2θ using Cu Kα radiation. Form F optionally can be characterized by an X-ray powder diffraction pattern having peaks shown in Table 8 set forth in the Examples. In some embodiments, Form F has an X-ray powder diffraction pattern substantially as shown in FIG. 10, wherein by "substantially" is meant that the reported peaks can vary by about ±0.2°.

Crystalline Sodium Salt Form G

Figure 11:
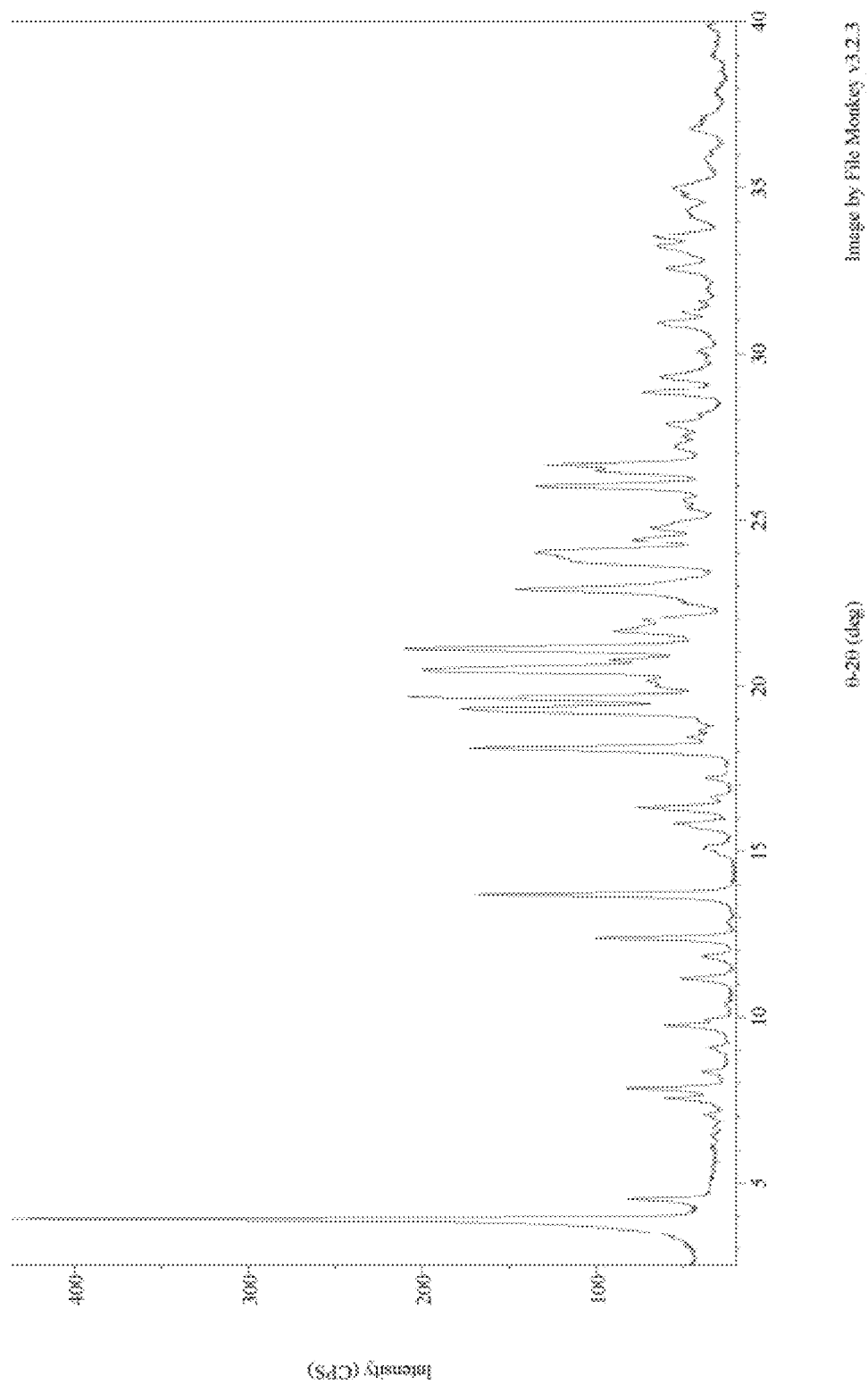
FIG. 11 depicts an X-ray powder diffraction ("XRPD") pattern of Compound 1 crystalline sodium salt Form G.

Crystalline form of Compound 1 sodium salt ("Form G") can be characterized by an X-ray powder diffraction pattern, obtained as set forth in the Examples, having peaks at about 3.93, 19.66, 20.48, and 21.10±0.2° 2θ using Cu Kα radiation. Form G optionally can 13.70, 18.12, 19.28, 22.90, 24.01, 25.99, and 26.64±0.2° 2θ using Cu Kα radiation. Form G optionally can be further characterized by an X-ray powder diffraction pattern having additional peaks at about 7.83, 12.37, 16.31, 20.17, 20.77, 21.62, 21.96, 24.41, 24.76, 26.45, 28.83, and 29.32±0.2° 2θ using Cu Kα radiation. Form G optionally can be characterized by an X-ray powder diffraction pattern having peaks shown in Table 9 set forth in the Examples. In some embodiments, Form G has an X-ray powder diffraction pattern substantially as shown in FIG. 11, wherein by "substantially" is meant that the reported peaks can vary by about ±0.2°.

Figure 12:
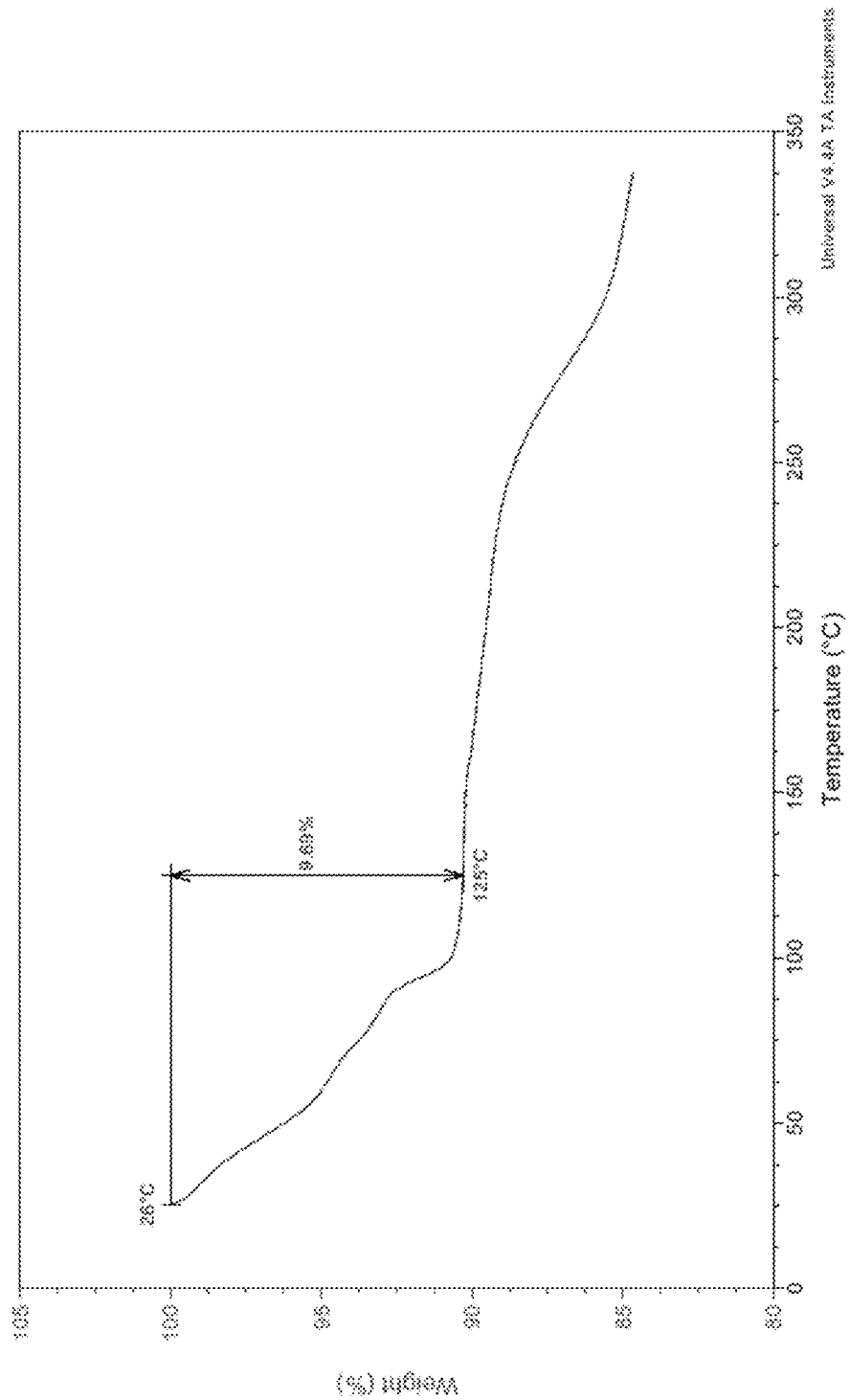
FIG. 12 depicts a thermogravimetric analysis ("TGA") trace of Compound 1 crystalline sodium salt Form G.

Form G also can be characterized by thermogravimetric analysis (TGA). Thus, Form G can be characterized by a weight loss in a range of about 5% to about 15% with an onset temperature in a range of about 25° C. to about 50° C. For example, Form G can be characterized by a weight loss of about 9.69%, up to about 125° C. In some embodiments, Form G has a thermogravimetric analysis substantially as depicted in FIG. 12, wherein by "substantially" is meant that the reported TGA features can vary by about ±5° C.

Crystalline Sodium Salt Form H

Figure 13:
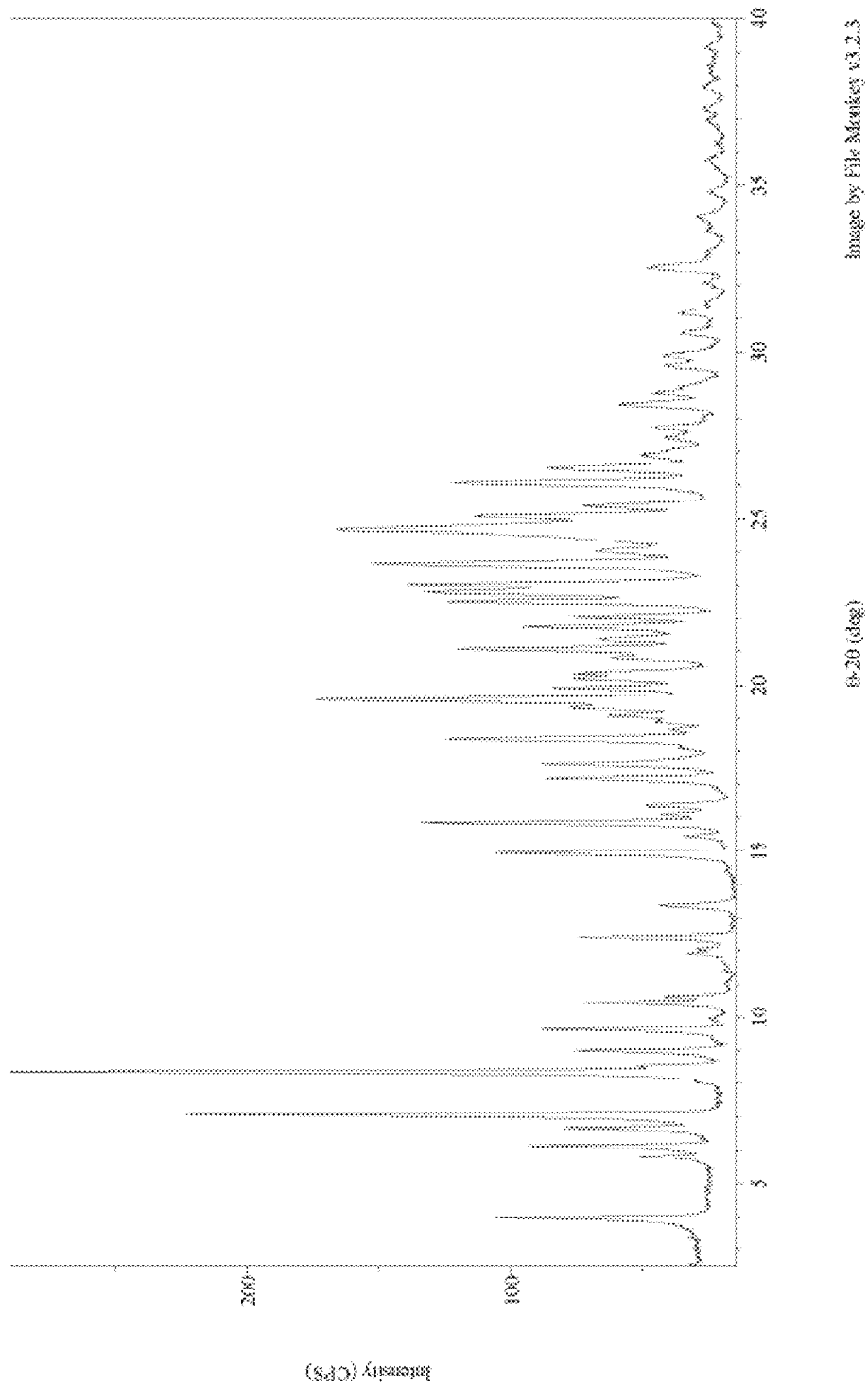
FIG. 13 depicts an X-ray powder diffraction ("XRPD") pattern of Compound 1 crystalline sodium salt Form H.

Crystalline form of Compound 1 sodium salt ("Form H") can be characterized by an X-ray powder diffraction pattern, obtained as set forth in the Examples, having peaks at about 7.09, 8.39, 19.56, 23.64, and 24.70±0.2° 2θ using Cu Kα radiation. Form H optionally can 4.01, 6.17, 14.94, 15.87, 18.38, 21.06, 22.51, 22.80, 23.02, and 26.05±0.2° 2θ using Cu Kα radiation. Form H optionally can be further characterized by an X-ray powder diffraction pattern having additional peaks at about 6.68, 9.00, 9.65, 10.46, 12.39, 19.07, 19.33, 19.94, 20.20, 20.38, 20.81, 21.35, 22.03, 24.04, 25.39, 26.48, and 28.42±0.2° 2θ using Cu Kα radiation. Form H optionally can be characterized by an X-ray powder diffraction pattern having peaks shown in Table 10 set forth in the Examples. In some embodiments, Form H has an X-ray powder diffraction pattern substantially as shown in FIG. 13, wherein by "substantially" is meant that the reported peaks can vary by about ±0.2°.

Figure 14:
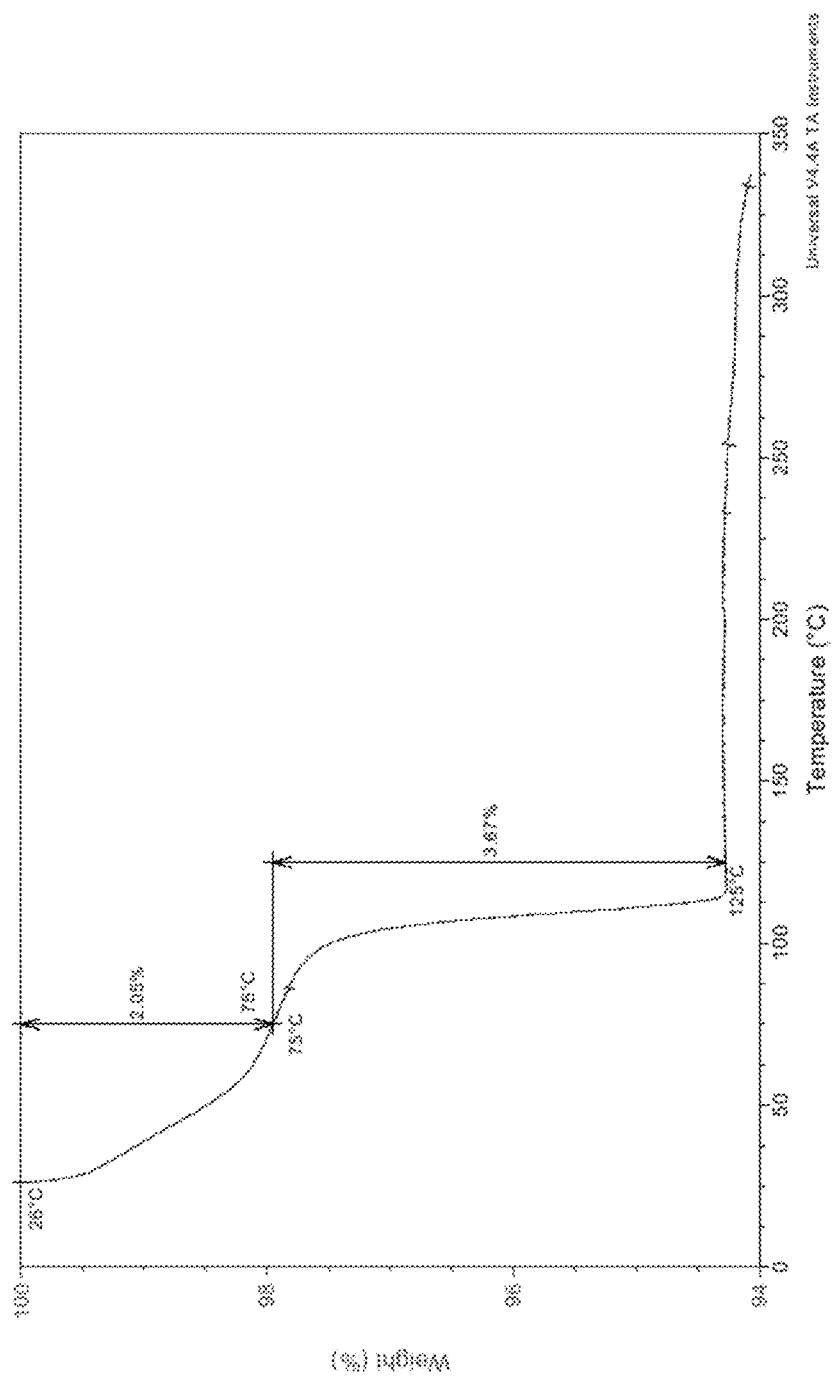
FIG. 14 depicts a thermogravimetric analysis ("TGA") trace of Compound 1 crystalline sodium salt Form H.

Differential scanning calorimetry (DSC) thermographs were obtained, as set forth in the Examples, for Form H. The DSC curve indicates an endothermic transition at about 118° C.±3° C. and 193° C.±3° C. Thus, in some embodiments, Form H can be characterized by a DSC thermograph having a solid-solid transition endotherm with an onset in a range of about 205° C. to about 207° C. For example, in some embodiments Form H is characterized by DSC, as shown in FIG. 14.

Figure 15:
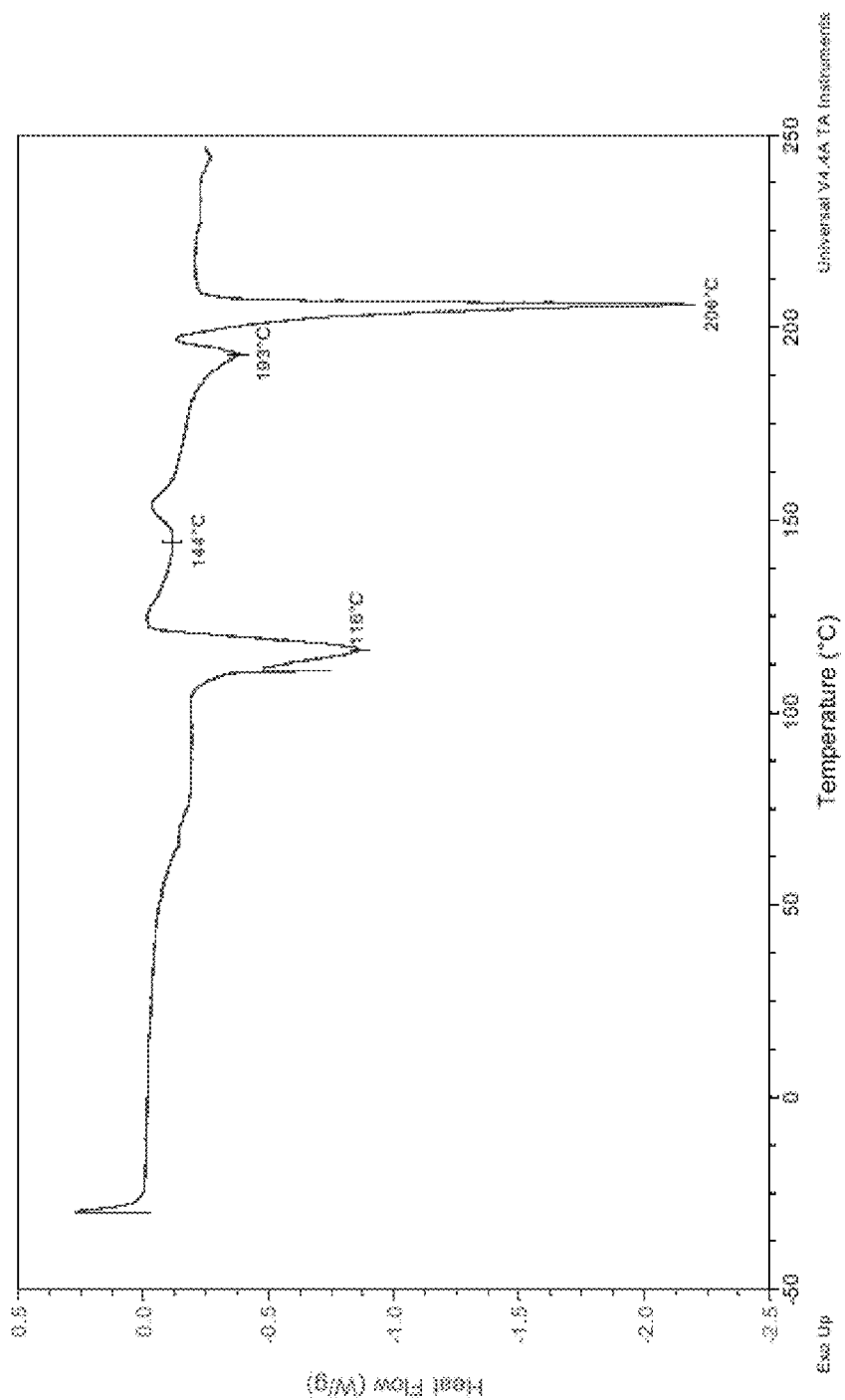
FIG. 15 depicts a differential scanning calorimetry ("DSC") thermograph of Compound 1 crystalline sodium salt Form H.

Form H also can be characterized by thermogravimetric analysis (TGA). Thus, Form H can be characterized by a weight loss in a range of about _% to about _% with an onset temperature in a range of about 30° C. to about 100° C. For example, Form H can be characterized by a weight loss of about 6%, up to about 125° C. In some embodiments, Form H has a thermogravimetric analysis substantially as depicted in FIG. 15, wherein by "substantially" is meant that the reported TGA features can vary by about ±5° C.

Pharmaceutical Compositions

Also provided herein are pharmaceutical compositions comprising a crystalline form of Compound 1 or a salt thereof described herein; and a pharmaceutically acceptable carrier. In embodiments, the carrier can comprise an excipient.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The compositions described herein can be formulated for any form of administration. In various cases, the composition is for oral administration. In various cases, the composition is in tablet form.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffers, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringers solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions as excipients.

Examples of pharmaceutically acceptable antioxidants as excipient include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

A pharmaceutical composition may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of an injectable pharmaceutical form may be brought about by the inclusion of agents which delay absorption such as aluminum monostearate and gelatin.

In some cases, in order to prolong the effect of one or more compounds provided herein, it is desirable to slow the absorption of the compound from subcutaneous or intramuscular injection. For example, delayed absorption of a parenterally administered compound can be accomplished by dissolving or suspending the compound in an oil vehicle.

The composition should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the methods of preparation are freeze-drying (lyophilization), which yields a powder of the active ingredient plus any additional desired ingredient from a previously sterile-filtered solution thereof.

Injectable depot forms can be made by forming microencapsule or nanoencapsule matrices of a compound provided herein in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes, microemulsions or nanoemulsions, which are compatible with body tissue.

In some embodiments, the polymorphs and salts disclosed herein are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811, which is incorporated herein by reference in its entirety.

The pharmaceutical compositions can be included in a container, pack, or dispenser together with instructions for administration.

Methods of Use

The uses of the salts and disclosed herein include use as an PDE4D inhibitor. The disclosed methods include inhibiting phosphodiesterase (PDE4D) by a method comprising contacting PDE4D with a salt or crystal disclosed herein in an amount effective to inhibit PDE4D. In some embodiments, the contacting is in vitro. In other aspects, the contacting is in vivo. In various embodiments, contacting comprises administering the salt or crystal to a subject in need thereof. In various embodiments, the subject is a mammal. In some embodiments, the mammalian subject is human.

A "therapeutically effective amount" means an amount effective to treat or to prevent development of, or to alleviate the existing symptoms of, the subject being treated. Determination of the effective amounts is well within the capability of those skilled in the art, especially in light of the detailed disclosure provided herein. Generally, a "therapeutically effective dose" refers to that amount of the salts or crystalline forms that results in achieving the desired effect. For example, in one preferred embodiment, a therapeutically effective amount of a salt or crystalline form disclosed herein decreases PDE4D activity by at least 5%, compared to control, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%.

The salts and crystalline forms disclosed herein can be useful for the treatment of certain diseases and disorders of the nervous system. Central nervous system disorders in which PDE4 inhibition may be useful include cortical dementias including Alzheimer's disease, AIDS-related dementia (HIV dementia), and mild cognitive impairment (MCI). Neurodegenerative disorders in which PDE4 inhibition may be useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia e.g. pre-senile dementia, and HIV-associated neurodegenerative disorder (HAND), cachexia, Sydenham's chorea, Huntington's disease, Parkinson's Disease, amyotrophic lateral sclerosis (ALS), Korsakoff's syndrome, and impairment relating to a cerebral vessel disorder. Further disorders in which PDE4 inhibition might prove useful include neuropathies of the central and peripheral nervous system, including, for example, IgA neuropathy, membranous neuropathy, idiopathic neuropathy, drug-induced peripheral neuropathy, diabetic neuropathy, HIV-associated neuropathy, and chronic inflammatory demyelinating polyneuropathy; as well as transverse myelitis, Guillain-Barre disease, encephalitis, and cancers of the nervous system. Compounds disclosed herein may also be used in the treatment of psychological disorders including anxiety, depression, major depressive disorder (MDD), bipolar disorder, and post-traumatic stress disorder. Salts and crystalline forms disclosed herein may also be used in the treatment of nervous system damage, for example that resulting from stroke, ischemias including cerebral ischemia (both focal ischemia, thrombotic stroke and global ischemia, for example, secondary to cardiac arrest and ischemic heart disease) and ischemia/reperfusion, ototoxicity and hearing loss, acute insults to the inner ear, including acoustic trauma, blast noise (for example, as experienced by military personnel), exposure to ototoxic chemotherapeutic agents for cancer therapy (such as cisplatin) and treatment with aminoglycoside antibiotics and other nervous system trauma.

Furthermore, salts and crystalline forms disclosed herein can be used in the treatment or prevention of opiate tolerance in patients needing protracted opiate analgesics, and benzodiazepine tolerance in patients taking benzodiazepines, and other addictive behavior, for example, nicotine addiction, alcoholism, and eating disorders. Moreover, the salts and crystalline forms can be useful in the treatment or prevention of drug withdrawal symptoms, for example treatment or prevention of symptoms of withdrawal from opiate, alcohol, or tobacco addiction.

Salts and crystalline forms disclosed herein can also be used in the treatment of acute and chronic pain and inflammation. They can be useful to treat patients with neuropathy, neuropathic pain, or inflammatory pain such as reflex sympathetic dystrophy/causalgia (nerve injury), peripheral neuropathy (including diabetic neuropathy), intractable cancer pain, complex regional pain syndrome, and entrapment neuropathy (carpel tunnel syndrome). They can also be useful in the treatment of pain associated with acute herpes zoster (shingles), postherpetic neuralgia (PHN), and associated pain syndromes such as ocular pain. They can further be useful as analgesics in the treatment of pain such as surgical analgesia, or as an antipyretic for the treatment of fever. Pain indications include, but are not limited to, post-surgical pain for various surgical procedures including post-cardiac surgery, dental pain/dental extraction, pain resulting from cancer, muscular pain, mastalgia, pain resulting from dermal injuries, lower back pain, headaches of various etiologies, including migraine, and the like. The salts and crystalline forms can also be useful for the treatment of pain-related disorders such as tactile allodynia and hyperalgesia. The pain may be somatogenic (either nociceptive or neuropathic), acute and/or chronic. The PDE4 inhibitors can also be useful in conditions where NSAIDs, morphine or fentanyl opiates and/or other opioid analgesics would traditionally be administered.

In addition, salts and crystalline forms disclosed herein can be used in the treatment of insulin resistance and other metabolic disorders such as atherosclerosis that are typically associated with an exaggerated inflammatory signaling.

Salts and crystalline forms disclosed herein can also be used in the treatment of respiratory disease or conditions, including therapeutic methods of use in medicine for preventing and treating a respiratory disease or condition including: asthmatic conditions including allergen-induced asthma, exercise-induced asthma, pollution-induced asthma, cold-induced asthma, and viral-induced-asthma; asthma-related diseases such as airway hyperreactivity and small airway disease; chronic obstructive pulmonary diseases including chronic bronchitis with normal airflow, chronic bronchitis with airway obstruction (chronic obstructive bronchitis), emphysema, asthmatic bronchitis, and bullous disease; and other pulmonary diseases involving inflammation including bronchiolitis, bronchioectasis, cystic fibrosis, pigeon fancier's disease, farmer's lung, acute respiratory distress syndrome, pneumonia, pneumonitis, aspiration or inhalation injury, fat embolism in the lung, acidosis inflammation of the lung, acute pulmonary edema, acute mountain sickness, acute pulmonary hypertension, persistent pulmonary hypertension of the newborn, perinatal aspiration syndrome, hyaline membrane disease, acute pulmonary thromboembolism, heparin-protamine reactions, sepsis, status asthamticus, hypoxia, dyspnea, hypercapnea, hyperinflation, hypoxemia, and cough.

Further, salts and crystalline forms disclosed herein can be used in the treatment of allergic disorders such as delayed type hypersensitivity reaction, allergic contact dermatitis, allergic rhinitis, and chronic sinusitis.

Salts and crystalline forms disclosed herein can also be used in the treatment of inflammation and related disorders. They can be useful as anti-inflammatory agents with the additional benefit of having significantly less harmful side effects. They can be useful to treat arthritis, including but not limited to rheumatoid arthritis, spondyloarthropathies, gouty arthritis, osteoarthritis, juvenile arthritis, acute rheumatic arthritis, enteropathic arthritis, neuropathic arthritis, psoriatic arthritis, reactive arthritis (Reiter's syndrome), and pyogenic arthritis, and autoimmune diseases, including systemic lupus erythematosus, hemolytic syndromes, autoimmune hepatitis, autoimmune neuropathy, vitiligo (autoimmune thyroiditis), Hashimoto's thyroiditis, anemias, myositis including polymyositis, alopecia greata, Goodpasture's syndrome, hypophytis, and pulmonary fibrosis.

Salts and crystalline forms disclosed herein can also be used in the treatment of osteoporosis and other related bone disorders.

Salts and crystalline forms disclosed herein can also be used in the treatment of gastrointestinal conditions such as reflux esophagitis, diarrhea, inflammatory bowel disease, Crohn's disease, gastritis, irritable bowel syndrome, Grave's disease (hyperthyroidism), necrotizing enterocolitis, and ulcerative colitis. They can also be used in the treatment of pulmonary inflammation, such as that associated with viral infections and cystic fibrosis.

In addition, salts and crystalline forms can also be useful in organ transplant patients either alone or in combination with conventional immunomodulators. Examples of conditions to be treated in said patients include graft vs. host reaction (i.e., graft vs. host disease), allograft rejections (e.g., acute allograft rejection, and chronic allograft rejection), transplant reperfusion injury, and early transplantation rejection (e.g., acute allograft rejection).

Yet further, the salts and crystalline forms can be useful in the treatment of pruritus and vitiligo.

Salts and crystalline forms disclosed herein can also be used in the treatment of tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephritis, nephrotic syndrome, Langerhan's cell histiocytosis, glomerulonephritis, reperfusion injury, pancreatitis, interstitial cystitis, Behcet's syndrome, polymyositis, gingivitis, periodontis, hypersensitivity, swelling occurring after injury, ischemias including myocardial ischemia, cardiovascular ischemia, and ischemia secondary to cardiac arrest, cirrhosis, septic shock, endotoxic shock, gram negative sepsis, toxic shock syndrome, stroke, ischemia reperfusion injury, multi-organ dysfunction, restenosis including restenosis following coronary bypass surgery, and the like.

Furthermore, the salts and crystalline forms disclose herein can also be useful in inhibiting PDE4 activity for the amelioration of systemic disorders including systemic hypotension associated with septic and/or toxic hemorrhagic shock induced by a wide variety of agents; as a therapy with cytokines such as TNF, IL-1 and IL-2; and as an adjuvant to short term immunosuppression in transplant therapy.

Salts and crystalline forms disclosed herein can also be used in the treatment of cancer, such as colorectal cancer, and cancer of the breast, lung, prostate, bladder, cervix and skin. They can be used in the treatment and prevention of neoplasias including but not limited to brain cancer, bone cancer, leukemia, lymphoma, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. The neoplasia can be selected from gastrointestinal cancer, liver cancer, bladder cancer, pancreas cancer, ovary cancer, prostate cancer, cervical cancer, lung cancer, breast cancer and skin cancer, such as squamous cell and basal cell cancers. The present salts and crystalline forms and methods can also be used to treat the fibrosis which occurs with radiation therapy. The present salts and crystalline forms and methods can be used to treat subjects having adenomatous polyps, including those with familial adenomatous polyposis (FAP). Additionally, the present salts and crystalline forms and methods can be used to prevent polyps from forming in patients at risk of FAP.

Salts and crystalline forms disclosed herein can also be used in the treatment of otic diseases and otic allergic disorders, including eustachian tube itching.

Salts and crystalline forms disclosed herein can also be used in the treatment of ophthalmic diseases.

Moreover, salts and crystalline forms disclosed herein can be used in the treatment of menstrual cramps, dysmenorrhea, premature labor, endometriosis, tendonitis, bursitis, skin-related conditions such as psoriasis, eczema, burns, sunburn, dermatitis, pancreatitis, hepatitis, lichen planus, scleritis, scleroderma, dermatomyositis, and the like. Other conditions in which the salts and crystalline forms of the subject invention can be used include diabetes (type I or type II), atherosclerosis, congestive heart failure, myocarditis, atherosclerosis, cerebral ischemia, angiogenesis, pulmonary hypertension, and aortic aneurysm.

The salts and crystalline forms disclosed herein can also be used in co-therapies, partially or completely, in place of other conventional anti-inflammatory therapies, such as together with steroids, NSAIDs, COX-2 selective inhibitors, 5-lipoxygenase inhibitors, LTB4 antagonists and LTA4 hydrolase inhibitors. Additional co-therapies comprising the compounds disclosed herein with biologics include: tumor necrosis factor alpha (TNFα) blockers such as etanercept (Enbrel), infliximab (Remicade), adalimumab (Humira), certolizumab pegol (Cimzia), and golimumab (Simponi); Interleukin 1 (IL-1) blockers such as anakinra (Kineret); monoclonal antibodies against B cells such as rituximab (Rituxan); T cell costimulation blocker such as abatacept (Orencia); and Interleukin 6 (IL-6) blockers such as tocilizumab (RoActemra or Actemra, an anti-IL-6 receptor antibody).

Salts and crystalline forms disclosed herein can also be used to prevent tissue damage when therapeutically combined with antibacterial or antiviral agents. In certain embodiments, the salts and crystalline forms disclosed herein can be combined with neuraminidase inhibitors for the treatment of a viral disease such as influenza.

Besides being useful for human treatment, salts and crystalline forms disclosed herein can also be useful for veterinary treatment of companion animals, exotic animals and farm animals, including mammals, rodents, and the like. More preferred animals include horses, dogs, and cats.

EXAMPLES

Methods
X-Ray Powder Diffraction (XRPD)

In various embodiments, XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

XRPD patterns acquired in the mother liquor were collected with an Inel XRG-3000 diffractometer. An incident beam of Cu Kα radiation was produced using a fine-focus tube and a parabolically graded multilayer mirror. Prior to the analysis, a silicon specimen (NIST SRM 640d) was analyzed to verify the observed position of the Si 111 peak is consistent with the NIST-certified position. An aliquot of the slurry sample was placed into a thin-walled glass capillary and centrifuged down, and a beam-stop was used to minimize the background from air. Diffraction patterns were collected in transmission geometry using Windif v. 6.6 software and a curved position-sensitive Equinox detector with a 2θ range of 120°.

The XRPD patterns of some embodiments were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640d) was analyzed to verify the observed position of the Si 111 peak is consistent with the NIST-certified position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (XCelerator) located 240 mm from the sample and Data Collector software v. 2.2b.

Differential Scanning calorimetry (DSC)

DSC was performed using a TA Instruments Q2000 differential scanning calorimeter. Temperature calibration was performed using NIST-traceable indium metal. The sample was placed into an aluminum DSC pan, covered with a lid, and the weight was accurately recorded. A weighed aluminum pan configured as the sample pan was placed on the reference side of the cell. The pans used were Tzero crimped pans, abbreviated "TOC" in the comments field on the thermogram. The sample was heated from −30° C. to 250° C., at 10° C./min (abbreviated "(−30)–250–10 in the Method field on the thermogram).

Thermal Gravimetric Analysis (TGA)

TGA was performed using a TA Instruments 2050 thermogravimetric analyzer. Temperature calibration was performed using nickel and Alumel™. The sample was placed in a platinum pan and inserted into the TG furnace. The furnace was heated under a nitrogen purge. The sample was heated from ambient temperature to 350° C. at 10° C./min.

Dynamic Vapor Sorption (DVS)

DVS data were collected on a VTI SGA-100 Vapor Sorption Analyzer. NaCl and PVP were used as calibration standards. The sample was not dried prior to analysis. Sorption and desorption data were collected over a range from 5% to 95% RH at 10% RH increments under a nitrogen purge. The equilibrium criterion used for analysis was less than 0.0100% weight change in five minutes with a maximum equilibration time of three hours. Data were not corrected for the initial moisture content of the samples.

Free base Crystalline Forms A-C: Free base crystalline Forms A, B and C were prepared by a stable form screening. The screening was comprised of 23 slurry experiments conducted using 22 different solvent systems, as summarized in Table 1 below. Various solvent systems were used including acetone, acetone and water, acetonitrile, acetonitrile and water, dichloromethane, p-dioxane, ether ($Et_2O$), ethyl acetate (EtOAc), ethanol (EtOH), ethanol and water, isopropyl alcohol (IPA), IPA and water, methyl isobutyl ketone (MIBK) and heptane, methyl ethyl ketone (MEK), methanol (MeOH), methyl tent-butyl ether (MTBE), tetrahydrofuran (THF), toluene, and toluene and heptane. The ratios of the solvent systems are detailed in Table 1 below.

The conditions of crystallization, major observations during the experiments, and results are also detailed in Table 1 below. The bulk of the experiments, 17, were conducted at room temperature (RT). Four experiments were performed in a cold room maintained at 2-8° C., and one experiment was conducted at 59° C. A final experiment was started at 59° C.; however, the sample dissolved and was cooled to ambient temperature. The sample was harvested when precipitation was observed and is therefore considered a precipitation experiment rather than a slurry experiment.

Sixteen experiments resulted in Form A without other materials, based on XRPD data, including three of the sub-ambient temperature experiments and both of the elevated temperature experiments. Five samples were primarily composed of Form A by XRPD; however, extra peaks (pks) were present in the patterns indicative of at least two extra materials.

The slurry in p-dioxane at ambient temperature quickly became a solid plug with little or no free solvent. XRPD analysis revealed a unique XRPD pattern and was designated Form B. The unit cell volume of the indexing solution was consistent with a mono-dioxane solvate. This result combined with the manner in which the sample formed Form B, a p-dioxane solvate. Finally, the ambient temperature dichloromethane (DCM) slurry resulted in a new material, Form C. The XRPD pattern of Form C was successfully indexed, and the indexed unit cell volume was consistent with a mono-DCM solvate. The sample was analyzed using TGA, and the 11.1 wt % loss at 100° C. is consistent with the sample being solvated. This weight loss corresponds to approximately 0.6 moles of DCM. Form C was observed to desolvate to Form A, both under ambient temperature vacuum for one day and under ambient temperature storage conditions for seven days. B/E, as used in the below tables, indicates a birefringent with extinction.

TABLE 1

| Solvent | Conditions [a] | Observations/Comments | XRPD Result |
|---|---|---|---|
| Acetone | 2-8° C., 13 days | — | Form A |
| 6:4 Acetone/$H_2O$ | RT, 4 days | Analyzed in mother liquor | Form A |
|  | RT, 12 days | Analyzed in mother liquor | Form A |
|  | RT, 20 days | Analyzed in mother liquor | Form A [b] |
| 7:3 Acetone/$H_2O$ | RT, 14 days | Analyzed in mother liquor | Diffuse scatter w/pks |
|  |  | — | Form A + pks |
| 98:2 Acetone/$H_2O$ | RT, 8 days | Little/no free solvent | Form A |
| ACN | RT, 14 days | — | Form A |
| 9:1 ACN/$H_2O$ | RT, 13 days | Analyzed in mother liquor | Form A |
| 95:5 ACN/$H_2O$ | RT, 14 days | Analyzed in mother liquor | Form A |
| DCM | 2-8° C., 13 days | — | A + pks |
|  |  | Analyzed 19 days after initial analysis, RT storage. | A + pks, smaller |
| DCM | RT, 3 days | Analyzed in mother liquor | Form C, shifting |
|  | RT, 5 days | Solvent removed/dried | Form C |
|  | RT, 12 days |  | A + pk at ~18° |
| p-Dioxane | RT, few minutes [c] | Quickly became solid plug w/little or no free | Form B |
| $Et_2O$ | RT, 9 days | Little/no free solvent; damp | A + pk at ~18° |
| EtOAc | RT, 13 days | Little/no free solvent; damp | A + pks |
| EtOH | RT, 14 days | — | Form A |
| 45:20 EtOH/$H_2O$ | RT, 13 days | Analyzed in mother liquor | Form A |
| IPA | RT, 14 days | — | Form A |
| 5:3 IPA/$H_2O$ [d] | 59° C.-RT | Small needles; B/E | Form A |
| 1:1 | RT, 14 days | Little/no free solvent; damp | A + pks |
| MIBK/Heptane |  | Analyzed 20 days after initial analysis, RT storage. | A + pks, smaller |

TABLE 1-continued

| Solvent | Conditions [a] | Observations/Comments | XRPD Result |
|---|---|---|---|
| MEK | RT, 12 days [e] | — | Form A |
| MeOH | 2-8° C., 13 days | — | Form A |
| MTBE | RT, 12 days [e] | Little/no free solvent; damp | Form A |
| THF | 2-8° C., 9 days | — | Form A |
| Toluene | RT, 9 days | Little/no free solvent; damp | Form A |
| 2:1 Toluene/Heptane [f] | 59° C. | Plates, blades, small needles; B/E | Form A |

[a] Times are approximate.
[b] Analysis is non-cGMP because of incorrect documentation.
[c] Initially clear sample stirred at 2-8° C. for 1 day, resulting in solid with apparently no solvent. Clear solution observed when warmed to RT. Solid BPN14770 was added, and the sample was stirred at RT. No solids were present after 3 days. Solid BPN14770 was added, the sample was slurried at RT, and the sample was observed to be a solid plug within a few minutes.
[d] Slurried in IPA 1 day, resulting in clear solution. BPN14770 added and slurried 1 day. Clear solution resulted. Water was added, resulting in thick solids. IPA added and slurried 1 day, resulting in clear solution. Cooled to RT. Transferred to larger vial after 4 days, resulting in precipitation. Thus, this experiment is considered a precipitation experiment rather than a slurry experiment.
[e] Initially clear sample stirred at 2-8° C. for 1 day. When precipitation was not observed, solid BPN14770 was added, and the sample was slurried at RT.
[f] Slurried in toluene 1 day, resulting in clear solution. BPN14770 added and slurried 1 day. Clear solution resulted. Heptane was added, resulting in the presence of solids. Slurried 4 days, part of the time without agitation.

The free base crystalline Form A was characterized by an XRPD pattern comprising peaks in Table 2.

TABLE 2

| 2θ (°) | d-spacing (Å) | Intensity (%) |
|---|---|---|
| 4.63 ± 0.20 | 19.068 ± 0.823 | 43 |
| 8.24 ± 0.20 | 10.725 ± 0.260 | 32 |
| 9.29 ± 0.20 | 9.514 ± 0.204 | 34 |
| 12.15 ± 0.20 | 7.281 ± 0.119 | 16 |
| 12.72 ± 0.20 | 6.952 ± 0.109 | 64 |
| 13.97 ± 0.20 | 6.336 ± 0.090 | 13 |
| 15.90 ± 0.20 | 5.569 ± 0.070 | 100 |
| 16.57 ± 0.20 | 5.347 ± 0.064 | 18 |
| 16.97 ± 0.20 | 5.219 ± 0.061 | 20 |
| 17.40 ± 0.20 | 5.092 ± 0.058 | 41 |
| 18.65 ± 0.20 | 4.755 ± 0.051 | 18 |
| 19.39 ± 0.20 | 4.574 ± 0.047 | 50 |
| 19.85 ± 0.20 | 4.469 ± 0.045 | 38 |
| 20.07 ± 0.20 | 4.420 ± 0.044 | 45 |
| 20.80 ± 0.20 | 4.266 ± 0.041 | 66 |
| 20.98 ± 0.20 | 4.230 ± 0.040 | 80 |
| 21.19 ± 0.20 | 4.189 ± 0.039 | 23 |
| 21.59 ± 0.20 | 4.113 ± 0.038 | 16 |
| 22.23 ± 0.20 | 3.996 ± 0.036 | 8 |
| 22.84 ± 0.20 | 3.890 ± 0.034 | 38 |
| 23.15 ± 0.20 | 3.839 ± 0.033 | 79 |
| 23.89 ± 0.20 | 3.722 ± 0.031 | 12 |
| 24.20 ± 0.20 | 3.674 ± 0.030 | 29 |
| 25.10 ± 0.20 | 3.546 ± 0.028 | 37 |
| 25.55 ± 0.20 | 3.484 ± 0.027 | 26 |
| 25.82 ± 0.20 | 3.448 ± 0.026 | 16 |
| 26.08 ± 0.20 | 3.414 ± 0.026 | 57 |
| 26.90 ± 0.20 | 3.311 ± 0.024 | 8 |
| 27.47 ± 0.20 | 3.244 ± 0.023 | 37 |
| 28.14 ± 0.20 | 3.169 ± 0.022 | 20 |
| 28.81 ± 0.20 | 3.096 ± 0.021 | 8 |
| 29.27 ± 0.20 | 3.049 ± 0.020 | 8 |
| 29.57 ± 0.20 | 3.019 ± 0.020 | 7 |

The free base crystalline Form B was characterized by an XRPD pattern comprising peaks in Table 3.

TABLE 3

| 2θ (°) | d-spacing (Å) | Intensity (%) |
|---|---|---|
| 4.90 ± 0.20 | 18.015 ± 0.735 | 47 |
| 6.87 ± 0.20 | 12.856 ± 0.374 | 13 |
| 9.40 ± 0.20 | 9.401 ± 0.200 | 9 |
| 9.82 ± 0.20 | 8.998 ± 0.183 | 8 |
| 12.59 ± 0.20 | 7.024 ± 0.111 | 8 |
| 13.26 ± 0.20 | 6.673 ± 0.100 | 9 |
| 13.49 ± 0.20 | 6.560 ± 0.097 | 13 |
| 15.54 ± 0.20 | 5.699 ± 0.073 | 11 |
| 16.46 ± 0.20 | 5.381 ± 0.065 | 47 |
| 18.03 ± 0.20 | 4.916 ± 0.054 | 37 |
| 18.74 ± 0.20 | 4.731 ± 0.050 | 41 |
| 18.89 ± 0.20 | 4.695 ± 0.049 | 44 |
| 19.39 ± 0.20 | 4.574 ± 0.047 | 48 |
| 19.71 ± 0.20 | 4.501 ± 0.045 | 49 |
| 20.02 ± 0.20 | 4.431 ± 0.044 | 59 |
| 20.29 ± 0.20 | 4.373 ± 0.043 | 50 |
| 21.14 ± 0.20 | 4.200 ± 0.039 | 24 |
| 21.32 ± 0.20 | 4.164 ± 0.039 | 56 |
| 21.51 ± 0.20 | 4.128 ± 0.038 | 97 |
| 21.75 ± 0.20 | 4.084 ± 0.037 | 44 |
| 22.04 ± 0.20 | 4.030 ± 0.036 | 17 |
| 22.43 ± 0.20 | 3.960 ± 0.035 | 22 |
| 22.93 ± 0.20 | 3.876 ± 0.033 | 26 |
| 23.29 ± 0.20 | 3.816 ± 0.032 | 24 |
| 23.57 ± 0.20 | 3.771 ± 0.032 | 100 |
| 23.83 ± 0.20 | 3.731 ± 0.031 | 16 |
| 24.22 ± 0.20 | 3.672 ± 0.030 | 20 |
| 24.95 ± 0.20 | 3.566 ± 0.028 | 12 |
| 25.34 ± 0.20 | 3.512 ± 0.027 | 14 |
| 25.65 ± 0.20 | 3.470 ± 0.027 | 24 |
| 26.02 ± 0.20 | 3.421 ± 0.026 | 16 |
| 26.44 ± 0.20 | 3.368 ± 0.025 | 14 |
| 26.77 ± 0.20 | 3.328 ± 0.024 | 18 |
| 26.96 ± 0.20 | 3.304 ± 0.024 | 14 |
| 27.80 ± 0.20 | 3.207 ± 0.023 | 9 |
| 28.39 ± 0.20 | 3.141 ± 0.022 | 11 |
| 28.76 ± 0.20 | 3.102 ± 0.021 | 8 |
| 29.35 ± 0.20 | 3.041 ± 0.020 | 7 |

The free base crystalline Form C was characterized by an XRPD pattern comprising peaks in Table 4.

TABLE 4

| 2θ (°) | d-spacing (Å) | Intensity (%) |
|---|---|---|
| 4.59 ± 0.20 | 19.250 ± 0.839 | 66 |
| 7.82 ± 0.20 | 11.294 ± 0.288 | 16 |
| 9.20 ± 0.20 | 9.608 ± 0.208 | 12 |

TABLE 4-continued

| 2θ (°) | d-spacing (Å) | Intensity (%) |
|---|---|---|
| 9.50 ± 0.20 | 9.303 ± 0.195 | 31 |
| 10.50 ± 0.20 | 8.419 ± 0.160 | 16 |
| 13.00 ± 0.20 | 6.806 ± 0.104 | 50 |
| 14.81 ± 0.20 | 5.975 ± 0.080 | 11 |
| 16.44 ± 0.20 | 5.387 ± 0.065 | 36 |
| 17.05 ± 0.20 | 5.196 ± 0.060 | 16 |
| 18.01 ± 0.20 | 4.920 ± 0.054 | 49 |
| 18.38 ± 0.20 | 4.824 ± 0.052 | 34 |
| 19.09 ± 0.20 | 4.646 ± 0.048 | 66 |
| 19.38 ± 0.20 | 4.576 ± 0.047 | 15 |
| 20.11 ± 0.20 | 4.411 ± 0.043 | 47 |
| 20.87 ± 0.20 | 4.254 ± 0.040 | 14 |
| 21.13 ± 0.20 | 4.201 ± 0.039 | 38 |
| 21.36 ± 0.20 | 4.156 ± 0.038 | 15 |
| 21.74 ± 0.20 | 4.084 ± 0.037 | 100 |
| 22.27 ± 0.20 | 3.989 ± 0.035 | 52 |
| 22.51 ± 0.20 | 3.946 ± 0.035 | 36 |
| 22.80 ± 0.20 | 3.897 ± 0.034 | 46 |
| 23.82 ± 0.20 | 3.732 ± 0.031 | 55 |
| 24.11 ± 0.20 | 3.689 ± 0.030 | 50 |
| 24.63 ± 0.20 | 3.611 ± 0.029 | 17 |
| 24.87 ± 0.20 | 3.577 ± 0.028 | 15 |
| 25.90 ± 0.20 | 3.438 ± 0.026 | 26 |
| 26.27 ± 0.20 | 3.390 ± 0.025 | 29 |
| 26.96 ± 0.20 | 3.304 ± 0.024 | 21 |
| 28.46 ± 0.20 | 3.134 ± 0.022 | 34 |
| 28.79 ± 0.20 | 3.099 ± 0.021 | 14 |
| 29.80 ± 0.20 | 2.996 ± 0.020 | 14 |

Crystalline salt Forms D-H: Crystalline salt forms of D, E, F, G, and H were prepared as described here. Attempts were made to crystallize three Compound 1 salts—calcium, potassium, and sodium—for characterization, shown below in Table 5. Nine different forms were found, all of the samples were crystalline; however, all but three sodium attempt samples were disordered crystalline materials.

Two calcium salt attempts exhibited similar patterns in terms of peak positions, indicating the samples were composed of the same crystalline material, designated crystalline calcium salt Form D. The two potassium salt attempts were composed of the same material, designated crystalline potassium salt Form E. A second pattern from a potassium salt was found, made by the procedure in Table 5, and designated crystalline potassium salt Form F.

Two materials were observed by XRPD, and found to be crystalline sodium salts, Forms G and H, made by the procedures in Table 5. The XRPD patterns exhibited by the crystalline sodium salts were composed of well resolved peaks, typical for crystalline materials; therefore, they were further characterized thermally and using proton NMR spectroscopy. TGA analysis of Form G showed a weight loss of approximately 10% at 125° C., indicating the material is solvated or hydrated. An attempt to desolvate the material at approximately 60° C. under vacuum resulted in a disordered Form G. Based on these results, Form G was not further characterized. The initial Form H sample was analyzed by TGA. TGA of Form H indicated it is solvated or hydrated, showing an approximately 2% weight loss at 75° C. followed by a weight loss of approximately 4% from 75 to 125° C. Storing the sample at approximately 60° C. under vacuum for a day resulted in a sample with a slightly shifted Form H XRPD pattern. This sample showed a TGA weight loss of approximately 1% weight loss at 75° C. followed by approximately 3% from 75 to 125° C., indicating the sample remained hydrated or solvated. The DSC data revealed a series of endothermic transitions.

TABLE 5

| Salt | Procedure | Observations |
|---|---|---|
| Calcium Form D | 1. Compound 1 sodium salt in 10:1:1 MeOH/IPA/acetone at ET$^c$. | 1. Hazy |
| | 2. Equimolar CaCl$_2$ in MeOH added. | 2. Became cloudy |
| | 3. Stirred at ET ~15 min., then SC$^d$ to RT. Stirred at RT 1 day. | 3. Solids present |
| | 4. Filtered | 4. Solids present |
| | 5. Partially evaporated | 5. Solids present |
| | 6. H$_2$O added. | 6. Minimal change |
| | 7. Refrigerated, then slurried 2-8° C., 1 day | 7. UM$^e$; spots B/E$^b$ |
| Calcium Form D | 8. H$_2$O added to filtrate of the above calcium Form D | 8. Solids |
| | 9. Stirred at RT 1 day | 9. UM; a few spots B/E |
| Potassium Form E | 1. Compound 1 dissolved in Et$_2$O | 1. Clear, colorless solution |
| | 2. Molar equivalent aq. KOH added | 2. Small amount oily precipitate |
| | 3. Briefly sonicated | 3. White solids |
| | 4. Stirred ~15 minutes, at RT. Vacuum filtered | 4. Paste-like |
| | 5. Slurried in Et$_2$O, 1 day, at RT. Vacuum filtered | 5. Waxy/pasty |
| | 6. Dried under vacuum, 1 day. | 6. UM; B/E |
| Potassium Form F | 1. Compound 1 dissolved in Et$_2$O | 1. Clear, colorless solution |
| | 2. Molar equivalent or KOH in MeOH added | 2. Very slight haze |
| | 3. Et$_2$O added | 3. No precipitation |
| | 4. Stirred 2-8° C., 4 days. | 4. No solids |
| | 5. Freezer, 1 day | 5. No solids |
| | 6. Evaporated | 6. Oil; solid film on vial walls |
| | 7. Et$_2$O added; sonicated | 7. Oil solidified + broke apart |
| | 8. Slurried, RT, 1 day | 8. UM; spots B/E |
| | 9. Slurried, RT, 4 days | 9. UM; regions birefringent; wax-like |
| | 10. Vacuum, 42° C., 1 day | 10. UM; B/E |

TABLE 5-continued

| Salt | Procedure | Observations |
|---|---|---|
| Sodium Form G | 1. Compound 1 dissolved in Et$_2$O<br>2. Molar equivalent aq. NaOH added3. Stirred ~15 minutes, RT. Vacuum filtered | 1. Clear, colorless solution<br>2. Precipitation of white solids; slowly at 1$^{st}$ large amount in short time.<br>3. Fine needles; B/E |
| Disordered Sodium Form | 4. Sample of the above sodium Form G vaccuumed, 60-61° C., 1 day | 4. Needles; B/E |
| Sodium Form H | 1. Compound 1 dissolved in Et$_2$O<br>2. Molar equivalent aq. NaOH added<br>3. Stirred RT, 4 days. | 1. Clear, colorless solution<br>2. Precipitation; thick solids within short time.<br>3. UM; portions B/E |
| Sodium Form H | 4. Sample of the above sodium Form H was vacuumed, 59-61° C., 1 day | 4. White solids; UM; regions B/E |

$^a$Times are approximate.
$^b$B/E refers to a birefringent with extinction.
$^c$ET refers to elevated temperature between room temperature and 65° C. The solution is heated to temperatures between room temperature and 65° C. until the solution was clear and no longer cloudy.
$^d$SC refers to cooling the temperature of solution slowly.
$^e$UM refers to an undefined morphology The crystalline calcium salt Form D was characterized by an XRPD pattern comprising peaks in Table 6.

TABLE 6

| 2θ (°) | d-spacing (Å) | Intensity (%) |
|---|---|---|
| 5.41 ± 0.20 | 16.325 ± 0.603 | 50 |
| 6.10 ± 0.20 | 14.472 ± 0.474 | 66 |
| 6.49 ± 0.20 | 13.601 ± 0.418 | 41 |
| 7.70 ± 0.20 | 11.467 ± 0.297 | 40 |
| 8.60 ± 0.20 | 10.270 ± 0.238 | 34 |
| 9.17 ± 0.20 | 9.632 ± 0.210 | 100 |
| 10.86 ± 0.20 | 8.141 ± 0.149 | 26 |
| 12.84 ± 0.20 | 6.888 ± 0.107 | 25 |
| 13.43 ± 0.20 | 6.590 ± 0.098 | 22 |
| 15.03 ± 0.20 | 5.889 ± 0.078 | 20 |
| 15.46 ± 0.20 | 5.727 ± 0.074 | 31 |
| 15.68 ± 0.20 | 5.648 ± 0.072 | 45 |
| 16.32 ± 0.20 | 5.425 ± 0.066 | 23 |
| 17.80 ± 0.20 | 4.978 ± 0.055 | 20 |
| 18.13 ± 0.20 | 4.890 ± 0.054 | 26 |
| 19.00 ± 0.20 | 4.666 ± 0.049 | 22 |
| 19.51 ± 0.20 | 4.546 ± 0.046 | 24 |
| 19.86 ± 0.20 | 4.468 ± 0.045 | 42 |
| 20.45 ± 0.20 | 4.339 ± 0.042 | 20 |
| 20.83 ± 0.20 | 4.262 ± 0.040 | 19 |
| 21.62 ± 0.20 | 4.107 ± 0.038 | 31 |
| 21.84 ± 0.20 | 4.066 ± 0.037 | 31 |
| 22.03 ± 0.20 | 4.031 ± 0.036 | 32 |
| 22.82 ± 0.20 | 3.893 ± 0.034 | 21 |
| 23.57 ± 0.20 | 3.771 ± 0.032 | 35 |
| 23.75 ± 0.20 | 3.743 ± 0.031 | 31 |
| 24.53 ± 0.20 | 3.625 ± 0.029 | 32 |
| 25.67 ± 0.20 | 3.467 ± 0.027 | 36 |
| 26.46 ± 0.20 | 3.366 ± 0.025 | 48 |
| 27.67 ± 0.20 | 3.221 ± 0.023 | 14 |
| 27.92 ± 0.20 | 3.193 ± 0.022 | 15 |
| 28.89 ± 0.20 | 3.088 ± 0.021 | 21 |

The crystalline potassium salt Form E was characterized by an XRPD pattern comprising peaks in Table 7.

TABLE 7

| 2θ (°) | d-spacing (Å) | Intensity (%) |
|---|---|---|
| 3.02 ± 0.20 | 29.236 ± 1.936 | 53 |
| 3.88 ± 0.20 | 22.771 ± 1.174 | 100 |
| 4.95 ± 0.20 | 17.854 ± 0.722 | 36 |
| 5.75 ± 0.20 | 15.349 ± 0.533 | 34 |
| 6.07 ± 0.20 | 14.545 ± 0.479 | 50 |
| 6.86 ± 0.20 | 12.878 ± 0.375 | 42 |
| 7.01 ± 0.20 | 12.605 ± 0.359 | 47 |

TABLE 7-continued

| 2θ (°) | d-spacing (Å) | Intensity (%) |
|---|---|---|
| 7.79 ± 0.20 | 11.343 ± 0.291 | 32 |
| 8.32 ± 0.20 | 10.619 ± 0.255 | 84 |
| 8.87 ± 0.20 | 9.961 ± 0.224 | 29 |
| 9.12 ± 0.20 | 9.688 ± 0.212 | 37 |
| 9.51 ± 0.20 | 9.293 ± 0.195 | 39 |
| 9.77 ± 0.20 | 9.047 ± 0.185 | 25 |
| 10.44 ± 0.20 | 8.468 ± 0.162 | 27 |
| 12.19 ± 0.20 | 7.253 ± 0.119 | 27 |
| 13.24 ± 0.20 | 6.679 ± 0.100 | 24 |
| 14.85 ± 0.20 | 5.962 ± 0.080 | 32 |
| 15.63 ± 0.20 | 5.663 ± 0.072 | 43 |
| 16.08 ± 0.20 | 5.508 ± 0.068 | 27 |
| 16.36 ± 0.20 | 5.412 ± 0.066 | 29 |
| 17.10 ± 0.20 | 5.180 ± 0.060 | 35 |
| 17.30 ± 0.20 | 5.122 ± 0.059 | 33 |
| 18.35 ± 0.20 | 4.832 ± 0.052 | 41 |
| 19.00 ± 0.20 | 4.666 ± 0.049 | 42 |
| 19.64 ± 0.20 | 4.517 ± 0.046 | 47 |
| 20.22 ± 0.20 | 4.389 ± 0.043 | 47 |
| 21.08 ± 0.20 | 4.211 ± 0.039 | 42 |
| 21.79 ± 0.20 | 4.076 ± 0.037 | 38 |
| 22.03 ± 0.20 | 4.032 ± 0.036 | 40 |
| 22.60 ± 0.20 | 3.932 ± 0.034 | 43 |
| 22.93 ± 0.20 | 3.875 ± 0.033 | 42 |
| 23.61 ± 0.20 | 3.765 ± 0.031 | 45 |
| 24.71 ± 0.20 | 3.600 ± 0.029 | 52 |
| 25.29 ± 0.20 | 3.519 ± 0.027 | 36 |
| 25.99 ± 0.20 | 3.426 ± 0.026 | 36 |

The crystalline potassium salt Form F was characterized by an XRPD pattern comprising peaks in Table 8.

TABLE 8

| 2θ (°) | d-spacing (Å) | Intensity (%) |
|---|---|---|
| 3.8 ± 0.2 | 23.418 ± 1.242 | 86 |
| 7.1 ± 0.2 | 12.388 ± 0.347 | 57 |
| 7.5 ± 0.2 | 11.809 ± 0.315 | 83 |
| 8.6 ± 0.2 | 10.262 ± 0.238 | 100 |
| 9.4 ± 0.2 | 9.391 ± 0.199 | 48 |
| 10.3 ± 0.2 | 8.565 ± 0.166 | 32 |
| 11.2 ± 0.2 | 7.880 ± 0.140 | 28 |
| 11.5 ± 0.2 | 7.669 ± 0.133 | 29 |
| 13.1 ± 0.2 | 6.758 ± 0.103 | 26 |
| 13.7 ± 0.2 | 6.458 ± 0.094 | 28 |
| 14.0 ± 0.2 | 6.312 ± 0.090 | 38 |
| 15.0 ± 0.2 | 5.886 ± 0.078 | 26 |
| 16.1 ± 0.2 | 5.497 ± 0.068 | 30 |
| 17.2 ± 0.2 | 5.142 ± 0.059 | 42 |

TABLE 8-continued

| 2θ (°) | d-spacing (Å) | Intensity (%) |
|---|---|---|
| 17.7 ± 0.2 | 5.001 ± 0.056 | 40 |
| 18.1 ± 0.2 | 4.900 ± 0.054 | 67 |
| 18.6 ± 0.2 | 4.759 ± 0.051 | 44 |
| 19.5 ± 0.2 | 4.542 ± 0.046 | 37 |
| 20.3 ± 0.2 | 4.365 ± 0.042 | 40 |
| 20.8 ± 0.2 | 4.271 ± 0.041 | 41 |
| 21.1 ± 0.2 | 4.199 ± 0.039 | 42 |
| 21.5 ± 0.2 | 4.128 ± 0.038 | 38 |
| 22.1 ± 0.2 | 4.023 ± 0.036 | 40 |
| 23.5 ± 0.2 | 3.776 ± 0.032 | 55 |
| 25.9 ± 0.2 | 3.444 ± 0.026 | 30 |
| 28.7 ± 0.2 | 3.110 ± 0.021 | 23 |
| 29.4 ± 0.2 | 3.031 ± 0.020 | 20 |

The crystalline sodium salt Form G was characterized by an XRPD pattern comprising peaks in Table 9.

TABLE 9

| 2θ (°) | d-spacing (Å) | Intensity (%) |
|---|---|---|
| 3.93 ± 0.20 | 22.441 ± 1.140 | 100 |
| 4.53 ± 0.20 | 19.506 ± 0.861 | 19 |
| 7.07 ± 0.20 | 12.495 ± 0.353 | 9 |
| 7.54 ± 0.20 | 11.711 ± 0.310 | 14 |
| 7.83 ± 0.20 | 11.286 ± 0.288 | 19 |
| 8.37 ± 0.20 | 10.552 ± 0.252 | 9 |
| 9.08 ± 0.20 | 9.735 ± 0.214 | 8 |
| 9.75 ± 0.20 | 9.060 ± 0.185 | 14 |
| 9.92 ± 0.20 | 8.912 ± 0.179 | 9 |
| 11.19 ± 0.20 | 7.903 ± 0.141 | 12 |
| 11.84 ± 0.20 | 7.469 ± 0.126 | 9 |
| 12.37 ± 0.20 | 7.149 ± 0.115 | 23 |
| 13.70 ± 0.20 | 6.457 ± 0.094 | 39 |
| 15.13 ± 0.20 | 5.849 ± 0.077 | 9 |
| 15.85 ± 0.20 | 5.588 ± 0.070 | 13 |
| 16.31 ± 0.20 | 5.429 ± 0.066 | 18 |
| 16.62 ± 0.20 | 5.329 ± 0.064 | 8 |
| 17.18 ± 0.20 | 5.156 ± 0.060 | 9 |
| 18.12 ± 0.20 | 4.892 ± 0.054 | 40 |
| 18.45 ± 0.20 | 4.806 ± 0.052 | 11 |
| 18.64 ± 0.20 | 4.755 ± 0.051 | 9 |
| 19.28 ± 0.20 | 4.600 ± 0.047 | 41 |
| 19.66 ± 0.20 | 4.511 ± 0.045 | 48 |
| 20.17 ± 0.20 | 4.399 ± 0.043 | 16 |
| 20.48 ± 0.20 | 4.333 ± 0.042 | 46 |
| 20.77 ± 0.20 | 4.274 ± 0.041 | 21 |
| 21.10 ± 0.20 | 4.207 ± 0.039 | 48 |
| 21.62 ± 0.20 | 4.108 ± 0.038 | 21 |
| 21.96 ± 0.20 | 4.045 ± 0.036 | 17 |
| 22.90 ± 0.20 | 3.880 ± 0.033 | 34 |
| 24.01 ± 0.20 | 3.703 ± 0.030 | 31 |
| 24.41 ± 0.20 | 3.643 ± 0.029 | 18 |
| 24.76 ± 0.20 | 3.593 ± 0.029 | 16 |
| 25.57 ± 0.20 | 3.480 ± 0.027 | 11 |
| 25.99 ± 0.20 | 3.425 ± 0.026 | 31 |
| 26.45 ± 0.20 | 3.367 ± 0.025 | 23 |
| 26.64 ± 0.20 | 3.343 ± 0.025 | 30 |
| 27.19 ± 0.20 | 3.277 ± 0.024 | 13 |
| 27.87 ± 0.20 | 3.199 ± 0.023 | 14 |
| 28.83 ± 0.20 | 3.094 ± 0.021 | 17 |
| 29.32 ± 0.20 | 3.044 ± 0.020 | 15 |

The crystalline sodium salt Form H was characterized by an XRPD pattern comprising peaks in Table 10.

TABLE 10

| 2θ (°) | d-spacing (Å) | Intensity (%) |
|---|---|---|
| 4.01 ± 0.20 | 22.042 ± 1.100 | 36 |
| 5.84 ± 0.20 | 15.122 ± 0.517 | 17 |
| 6.17 ± 0.20 | 14.307 ± 0.463 | 31 |
| 6.68 ± 0.20 | 13.212 ± 0.395 | 27 |
| 7.09 ± 0.20 | 12.465 ± 0.351 | 76 |
| 8.39 ± 0.20 | 10.531 ± 0.251 | 100 |
| 8.54 ± 0.20 | 10.346 ± 0.242 | 18 |
| 9.00 ± 0.20 | 9.815 ± 0.218 | 25 |
| 9.65 ± 0.20 | 9.156 ± 0.189 | 30 |
| 9.95 ± 0.20 | 8.885 ± 0.178 | 8 |
| 10.46 ± 0.20 | 8.454 ± 0.161 | 24 |
| 10.65 ± 0.20 | 8.298 ± 0.155 | 14 |
| 11.91 ± 0.20 | 7.426 ± 0.124 | 11 |
| 12.05 ± 0.20 | 7.339 ± 0.121 | 10 |
| 12.39 ± 0.20 | 7.137 ± 0.115 | 25 |
| 13.37 ± 0.20 | 6.616 ± 0.099 | 15 |
| 14.94 ± 0.20 | 5.926 ± 0.079 | 36 |
| 15.46 ± 0.20 | 5.728 ± 0.074 | 12 |
| 15.87 ± 0.20 | 5.580 ± 0.070 | 45 |
| 16.11 ± 0.20 | 5.499 ± 0.068 | 15 |
| 16.37 ± 0.20 | 5.410 ± 0.066 | 17 |
| 17.15 ± 0.20 | 5.165 ± 0.060 | 30 |
| 17.63 ± 0.20 | 5.027 ± 0.057 | 31 |
| 18.38 ± 0.20 | 4.822 ± 0.052 | 43 |
| 18.66 ± 0.20 | 4.752 ± 0.050 | 14 |
| 18.90 ± 0.20 | 4.692 ± 0.049 | 15 |
| 19.07 ± 0.20 | 4.649 ± 0.048 | 22 |
| 19.33 ± 0.20 | 4.589 ± 0.047 | 27 |
| 19.56 ± 0.20 | 4.534 ± 0.046 | 60 |
| 19.94 ± 0.20 | 4.449 ± 0.044 | 29 |
| 20.20 ± 0.20 | 4.392 ± 0.043 | 26 |
| 20.38 ± 0.20 | 4.355 ± 0.042 | 26 |
| 20.81 ± 0.20 | 4.264 ± 0.041 | 21 |
| 21.06 ± 0.20 | 4.214 ± 0.040 | 41 |
| 21.35 ± 0.20 | 4.158 ± 0.038 | 23 |
| 21.72 ± 0.20 | 4.089 ± 0.037 | 32 |
| 22.03 ± 0.20 | 4.032 ± 0.036 | 26 |
| 22.51 ± 0.20 | 3.947 ± 0.035 | 42 |
| 22.80 ± 0.20 | 3.897 ± 0.034 | 45 |
| 23.02 ± 0.20 | 3.860 ± 0.033 | 48 |
| 23.64 ± 0.20 | 3.760 ± 0.031 | 52 |
| 24.04 ± 0.20 | 3.699 ± 0.030 | 23 |
| 24.70 ± 0.20 | 3.602 ± 0.029 | 57 |
| 25.09 ± 0.20 | 3.547 ± 0.028 | 38 |
| 25.39 ± 0.20 | 3.504 ± 0.027 | 25 |
| 26.05 ± 0.20 | 3.417 ± 0.026 | 42 |
| 26.48 ± 0.20 | 3.363 ± 0.025 | 29 |
| 26.92 ± 0.20 | 3.309 ± 0.024 | 17 |
| 27.43 ± 0.20 | 3.249 ± 0.023 | 14 |
| 27.74 ± 0.20 | 3.213 ± 0.023 | 15 |
| 28.42 ± 0.20 | 3.138 ± 0.022 | 20 |
| 28.76 ± 0.20 | 3.102 ± 0.021 | 15 |
| 29.60 ± 0.20 | 3.015 ± 0.020 | 14 |
| 29.91 ± 0.20 | 2.985 ± 0.020 | 14 |

What is claimed:

1. A crystalline form of free base Compound 1 (Form A), characterized by an X-ray powder diffraction (XRPD) pattern comprising peaks at 12.72, 15.90, 19.39, 20.80, 20.98, 23.15, and 26.08,±0.2° 2θ using Cu Kα radiation.

2. The crystalline form of claim 1, further characterized by XRPD pattern peaks at 4.63, 17.40, 19.85, 20.07, 22.84, 25.10, and 27.47, and optionally further comprising 8.24, 9.29, 16.97, 18.65, 21.19, 21.59, 23.89, 24.20, 25.55, 25.82, and 28.14±0.2° 2θ using Cu Kα radiation.

3. The crystalline form of claim 1, having an endothermic transition at 125° C. to 135° C., as measured by differential scanning calorimetry ("DSC").

4. The crystalline form of claim 3, wherein the endothermic transition is at 131° C.±3° C.

5. The crystalline form of claim 1, having a dynamic vapor sorption ("DVS") substantially as a shown in FIG. 4.

6. A crystalline form of Compound 1 selected from the group consisting of
   (a) Compound 1 and p-dioxane (Form B), characterized by an X-ray powder diffraction (XRPD) pattern comprising peaks at 20.02, 20.29, 21.32, 21.51, and 23.57, ±0.2° 2θ using Cu Kα radiation,
   (b) Compound 1 and dichloromethane (Form C), characterized by an X-ray powder diffraction (XRPD) pattern comprising peaks at 4.59, 13.00, 19.09, 21.74, 22.27, 23.82, and 24.11,±0.2° 2θ using Cu Kα radiation;
   (c) Compound 1 calcium salt (Form D), characterized by an X-ray powder diffraction (XRPD) pattern comprising peaks at 6.10, 9.17, 15.68, 19.86, and 26.46,±0.2° 2θ using Cu Kα radiation;
   (d) Compound 1 potassium salt (Form E), characterized by an X-ray powder diffraction (XRPD) pattern comprising peaks at 3.02, 3.88, 6.07, 7.01, and 8.32,±0.2° 2θ using Cu Kα radiation;
   (e) Compound 1 potassium salt (Form F), characterized by an X-ray powder diffraction (XRPD) pattern comprising peaks at 3.8, 7.1, 7.5, 8.6, 9.4, 18.1, and 23.5, ±0.2° 2θ using Cu Kα radiation;
   (f) Compound 1 sodium salt (Form G), characterized by an X-ray powder diffraction (XRPD) pattern comprising peaks at 3.93, 19.66, 20.48, and 21.10,±0.2° 2θ using Cu Kα radiation; and
   (b) Compound 1 sodium salt (Form H), characterized by an X-ray powder diffraction (XRPD) pattern comprising peaks at 7.09, 8.39, 19.56, 23.64, and 24.70,±0.2° 2θ using Cu Kα radiation.

7. The crystalline form of claim 6, wherein Compound 1 and p-dioxane (Form B) is further characterized by XRPD pattern peaks at 4.90, 16.46, 18.03, 18.74, 18.89, 19.39, 19.71, and 21.75, and optionally further comprising 18.03, 21.14, 22.43, 22.93, 23.29, 23.83, 24.22, 25.65, 26.02, and 26.77±0.2° 2θ using Cu Kα radiation.

8. The crystalline form of claim 6, wherein Compound 1 and dichloromethane (Form C) is further characterized by XRPD pattern peaks at 9.50, 16.44, 18.01, 18.38, 20.11, 21.13, 22.51, 22.80, and 28.46, and optionally further comprising 7.82, 9.20, 10.50, 14.81, 17.05, 19.38, 20.87, 21.36, 24.63, 24.87, 28.79, and 29.80±0.2° 2θ using Cu Kα radiation.

9. The crystalline form of claim 6, wherein the crystalline form of Compound 1 and dichloromethane (Form C) is a ratio of 1 to 1 of Compound 1 to dichloromethane.

10. The crystalline form of claim 6, wherein Compound 1 calcium salt (Form D) is further characterized by XRPD pattern peaks at 5.41, 6.49, 7.70, 8.60, 10.86, 12.84, 15.46, 15.68, 19.86, 21.62, 21.84, 22.03, 23.57, 23.75, 24.53, 25.67, and 26.46, and optionally further comprises 13.43, 15.03, 16.32, 17.80, 18.13, 19.00, 19.51, 20.45, 20.83, 22.82, and 28.89±0.2° 2θ using Cu Kα radiation.

11. The crystalline form of claim 6, wherein the Compound 1 potassium salt (Form E) is further characterized by XRPD pattern peaks at 6.86, 15.63, 18.35, 19.00, 19.64, 20.22, 21.08, 21.79, 22.03, 22.60, 22.93, 23.61, and 24.71, and optionally further comprises 7.79, 8.87, 9.12, 9.51, 9.77, 10.44, 12.19, 14.85, 16.08, 16.36, 17.10, 17.30, 25.29, and 25.99±0.2° 2θ using Cu Kα radiation.

12. The crystalline form of claim 6, wherein the Compound 1 potassium salt (Form F) is further characterized by XRPD pattern peaks at 10.3, 11.2, 11.5, 13.1, 13.7, 14.0, 15.0, 16.1, 17.2, 17.7, 18.6, 19.5, 20.3, 20.8, 21.1, 21.5, 22.1, 25.9, 28.7 and 29.4,±0.2° 2θ using Cu Kα radiation.

13. The crystalline form of claim 6, wherein Compound 1 sodium salt (Form G) is further characterized by XRPD pattern peaks at 13.70, 18.12, 19.28, 22.90, 24.01, 25.99, and 26.64, and optionally further comprises 4.53, 7.83, 12.37, 16.31, 20.17, 20.77, 21.62, 21.96, 24.41, 24.76, 26.45, 28.83, and 29.32±0.2° 2θ using Cu Kα radiation.

14. The crystalline form of claim 6, wherein Compound 1 sodium slat (Form H) is further characterized by XRPD pattern peaks at 4.01, 6.17, 14.94, 15.87, 18.38, 21.06, 22.51, 22.80, 23.02, and 26.05, and optionally further comprises 6.68, 9.00, 9.65, 10.46, 12.39, 19.07, 19.33, 19.94, 20.20, 20.38, 20.81, 21.35 22.03, 24.04, 25.39, 26.48, and 28.42±0.2° 2θ using Cu Kα radiation.

15. The crystalline form of claim 6, wherein Compound 1 sodium salt (Form H) has an endothermic transition at 110° C. to 120° C. and 200° C. to 210° C., as measured by differential scanning calorimetry ("DSC").

16. The crystalline form of claim 15, wherein the endothermic transition is at 116° C.±3° C. and 206° C.±3° C.

* * * * *

UNITED STATES PATENT AND TRADEMARK OFFICE
CERTIFICATE OF CORRECTION

| | |
|---|---|
| PATENT NO. | : 11,028,050 B2 |
| APPLICATION NO. | : 16/851203 |
| DATED | : June 8, 2021 |
| INVENTOR(S) | : Mark E. Gurney et al. |

It is certified that error appears in the above-identified patent and that said Letters Patent is hereby corrected as shown below:

In the Claims

At Column 22, Line 54, in Claim 1, ",±0.2°" should be -- ±0.2° -- at each occurrence throughout the claims.

At Column 22, Line 67, in Claim 5, "as a shown" should be -- as shown --.

At Column 23, Line 2, in Claim 6, "consisting of" should be -- consisting of: --.

At Column 23, Line 6, in Claim 6, "radiation," should be -- radiation; --.

At Column 23, Line 27, in Claim 6, "(b) Compound 1" should be -- (g) Compound 1 --.

At Column 24, Line 34, in Claim 14, "21.35 22.03," should be -- 21.35, 22.03, --.

Signed and Sealed this
Third Day of May, 2022

Katherine Kelly Vidal
*Director of the United States Patent and Trademark Office*